(12) United States Patent
Edwards et al.

(10) Patent No.: US 9,481,696 B1
(45) Date of Patent: Nov. 1, 2016

(54) THIOPHOSPHATES AND THIOPHOSPHATE DERIVATIVES AS LUBRICANT ADDITIVES

(71) Applicant: Afton Chemical Corporation, Richmond, VA (US)

(72) Inventors: David Edwards, Richmond, VA (US); Kristine Durbin, Mechanicsville, VA (US); Robert E. McCovick, Chesterfield, VA (US)

(73) Assignee: Afton Chemical Corporation, Richmind, VA (US)

( * ) Notice: Subject to any disclaimer, the term of this patent is extended or adjusted under 35 U.S.C. 154(b) by 0 days.

(21) Appl. No.: 14/830,719

(22) Filed: Aug. 19, 2015

(51) Int. Cl.
*C07F 9/165* (2006.01)
*C10M 163/00* (2006.01)

(52) U.S. Cl.
CPC ............ *C07F 9/165* (2013.01); *C10M 163/00* (2013.01)

(58) Field of Classification Search
CPC .............................. C07F 9/165; C10M 163/00
See application file for complete search history.

(56) References Cited

U.S. PATENT DOCUMENTS 5,132,031 A * 7/1992 Born ................... C07F 9/1651
252/389.2
5,306,436 A * 4/1994 Born ..................... C07F 9/091
508/370

* cited by examiner

*Primary Examiner* — Valerie Rodriguez-Garcia
(74) *Attorney, Agent, or Firm* — Brinks Gilson & Lione

(57) ABSTRACT

The present invention provides thiophosphates and thiophosphate derivatives useful as antiwear additive components, lubricant additive compositions and lubricant compositions each comprising such compounds, and methods for making and using the same. In one aspect, the invention relates to a compound of formula (I):

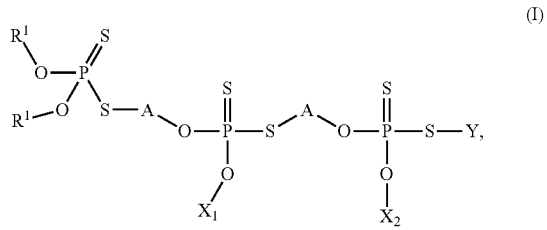

or a tribologically acceptable salt thereof.

30 Claims, No Drawings

THIOPHOSPHATES AND THIOPHOSPHATE DERIVATIVES AS LUBRICANT ADDITIVES

FIELD OF THE INVENTION

The invention relates to phosphorous-containing compounds useful as antiwear additive components, lubricant additive compositions and lubricant compositions each comprising such compounds, and methods for making and using the same.

BACKGROUND OF THE INVENTION

Traditionally, anti-wear components of lubricating compositions comprise acidic organophosphates salted with amines and/or metal ions. These components provide good anti-wear protection but other performance attributes can suffer including poor seal durability, reduced oxidative stability, and inadequate corrosion inhibition. Phosphorus- and sulfur-containing compounds are understood to be essential in lubricating fluids to protect surfaces from wear as a result of the extreme pressures encountered by the surfaces. As a result, these fluids have traditionally been harmful to seals (dynamic and static) and yellow metals. In addition, there is increasing pressure from regulatory agencies to remove amines and metal ions from lubricating fluids to decrease the environmental impact of such components. Due to these increasing environmental concerns, the presence of amines and metal ions in antiwear additives is becoming less desirable. Accordingly, there is a need to develop novel antiwear compounds contain little or no amines or metal ions.

BRIEF SUMMARY OF THE INVENTION

In one aspect, the invention relates to a compound of formula (I)

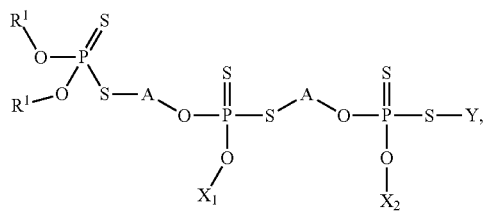

(I)

or a tribologically acceptable salt thereof,
wherein A is:

each $R^1$ is the same or different and is independently selected from alkyl, alkenyl, cycloalkyl, cycloalkylalkyl, aryl, and aralkyl, wherein said aryl and aralkyl are optionally substituted with one to three substituents each independently selected from alkyl and alkenyl;
each $R^2$ and $R^3$ are independently selected from H, alkyl, alkenyl, cycloalkyl and cycloalkylalkyl;
Y is selected from the group consisting of alkyl, alkoxyalkyl, benzyl, and $-R^4-R^5-R^6$;

$R^4$ is alkylene;
$R^5$ is selected from the group consisting of a bond, alkylene; —C(O)— and —C($R^7$)—;
$R^6$ is selected from the group consisting of alkyl, hydroxyalkyl, hydroxyalkyleneoxy, hydroxy and alkoxy;
$R^7$ is hydroxy;
m is an integer from 2 to 8;
$X_1$ is $R^8$ or Z;
$X_2$ is selected from the group consisting of $R^8$,

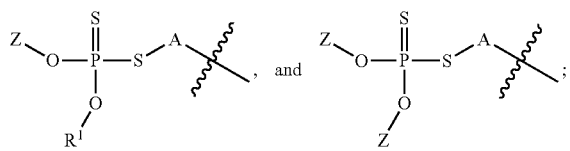

$R^8$ is alkyl, alkenyl, cycloalkyl, cycloalkylalkyl, aryl, and aralkyl, wherein said aryl and aralkyl are optionally substituted with one to three substituents each independently selected from alkyl and alkenyl; and
Z is,

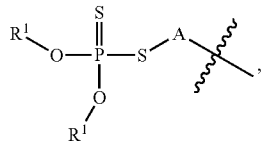

wherein when $X_2$ is $R^8$, $X_1$ is Z.

In a second aspect, the invention provides a lubricant additive composition comprising a compound of the present invention.

In a third aspect, the invention provides a lubricant composition comprising a major amount of an oil of lubricating viscosity or a grease prepared therefrom and a minor amount of the compound of the present invention.

In a fourth aspect, the invention provides a method of lubricating moving metal surfaces comprising lubricating the metal surfaces with a lubricant composition of the present invention.

In a fifth aspect, the present invention provides a compound prepared by a process comprising:
 a. reacting a phosphorodithioate with a first epoxide;
 b. reacting the product of step a) with a first phosphorodithioating agent;
 c. reacting the product of step b) with a second epoxide;
 d. reacting the product of step c) with a second phosphorodithioating agent; and
 e. reacting the product of step d) with a reactive group.

DETAILED DESCRIPTION OF THE INVENTION

The invention disclosed herein relates to novel phosphorous-containing compounds that are useful as antiwear agents and methods for preparing the same. The invention also provides lubricant additive compositions and lubricant compositions comprising the compounds, and methods of using the same.

The compounds of the present invention include compounds of formula (I)

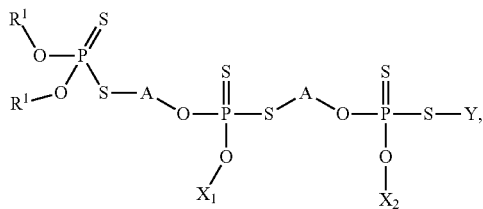

(I)

or a tribologically acceptable salt thereof,
wherein A is:

each $R^1$ is the same or different and is independently selected from alkyl, alkenyl, cycloalkyl, cycloalkylalkyl, aryl, and aralkyl, wherein said aryl and aralkyl are optionally substituted with one to three substituents each independently selected from alkyl and alkenyl;

each $R^2$ and $R^3$ are independently selected from H, alkyl, alkenyl, cycloalkyl and cycloalkylalkyl;

Y is selected from the group consisting of alkyl, alkoxyalkyl, benzyl, and —$R^4$-$R^5$-$R^6$;

$R^4$ is alkylene;

$R^5$ is selected from the group consisting of a bond, alkylene; —C(O)— and —C($R^7$)—;

$R^6$ is selected from the group consisting of alkyl, hydroxyalkyl, hydroxyalkyleneoxy, hydroxy and alkoxy;

$R^7$ is hydroxy;

m is an integer from 2 to 8;

$X_1$ is $R^8$ or Z;

$X_2$ is selected from the group consisting of $R^8$,

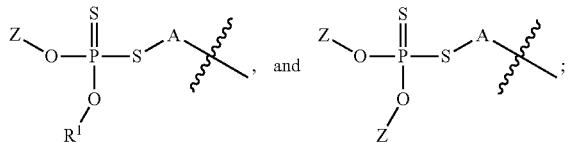

$R^8$ is alkyl, alkenyl, cycloalkyl, cycloalkylalkyl, aryl, and aralkyl, wherein said aryl and aralkyl are optionally substituted with one to three substituents each independently selected from alkyl and alkenyl; and Z is

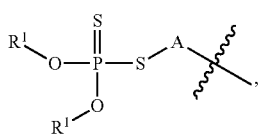

wherein when $X_2$ is $R^8$, $X_1$ is Z.

In one embodiment, each $R^1$ is the same or different and is independently selected from $C_1$-$C_{30}$alkyl, $C_1$-$C_{30}$alkenyl, cycloalkyl, cycloalkylalkyl, aryl and aralkyl, wherein said aryl and aralkyl are optionally substituted with one to three substituents each independently selected from $C_1$-$C_{10}$alkyl and $C_1$-$C_{10}$alkenyl.

In another embodiment, each $R^1$ is the same or different and is independently $C_3$-$C_{10}$alkyl.

In some embodiments, m is an integer from 2 to 5. In certain embodiments, m is 2.

In one embodiment, each $R^2$ and $R^3$ are independently selected from H and $C_1$-$C_{10}$alkyl. In another embodiment, for each instance of A, one $R^2$ is alkyl and the remaining instances of $R^2$ and $R^3$ are H. In a further embodiment, when $R^2$ is alkyl, the alkyl is $C_1$-$C_{10}$alkyl.

In a further embodiment, $X_2$ is

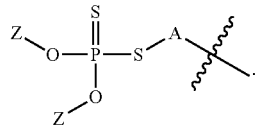

In another embodiment, $X_2$ is $R^8$.

In another embodiment, Y is —$R^4$-$R^5$-$R^6$. In a further embodiment, Y is —$R^4$-$R^5$-$R^6$ and $R^4$ is alkylene, $R^5$ is —C(O)—, and $R^6$ is hydroxy or alkoxy.

In one embodiment, $R^8$ is $C_1$-$C_{10}$ alkyl.

In one embodiment, each $R^1$ is independently selected from $C_1$-$C_{30}$ alkyl. In another embodiment, each $R^1$ is independently selected from $C_3$-$C_{10}$ alkyl. In another embodiment, each $R^1$ is independently selected from $C_3$-$C_6$ alkyl. In certain embodiments, each $R^1$ is the same as every other $R^1$.

In one embodiment, Y is $C_1$-$C_{20}$ alkyl.

In one embodiment, the invention provides a compound of formula (Ia)

Ia

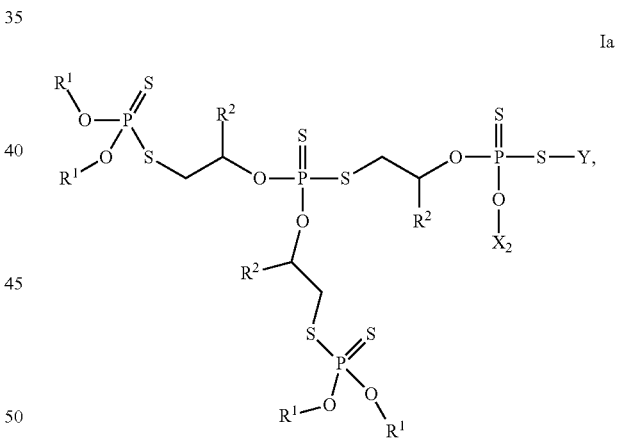

or a tribologically acceptable salt thereof, each $R^1$ is the same or different and is independently selected from alkyl, alkenyl, cycloalkyl, cycloalkylalkyl, aryl, and aralkyl, wherein said aryl and aralkyl are optionally substituted with one to three substituents each independently selected from alkyl and alkenyl;

each $R^2$ is independently selected from alkyl, alkenyl, cycloalkyl and cycloalkylalkyl; Y is selected from the group consisting of alkyl, alkoxyalkyl, benzyl, and —$R^4$-$R^5$-$R^6$;

$R^4$ is alkylene;

$R^5$ is selected from the group consisting of a bond, alkylene; —C(O)— and —C($R^7$)—;

$R^6$ is selected from the group consisting of alkyl, hydroxyalkyl, hydroxyalkyleneoxy, hydroxy and alkoxy;

$R^7$ is hydroxy;
$X_2$ is selected from the group consisting of $R^8$,
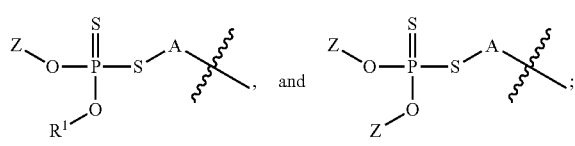
$R^8$ is alkyl, alkenyl, cycloalkyl, cycloalkylalkyl, aryl, and aralkyl, wherein said aryl and aralkyl are optionally substituted with one to three substituents each independently selected from alkyl and alkenyl; and
Z is
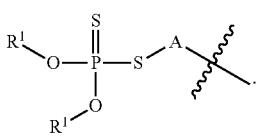
In one embodiment, the compound of formula I is selected from:
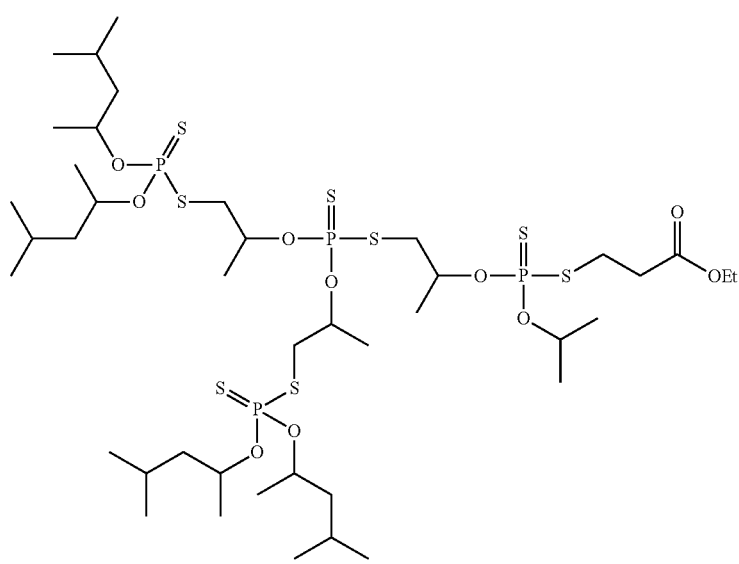 [SMILES: CCOC(=O)CCSP(=S)(OC(C)C)OC(C)CSP(=S)(OC(C)CSP(=S)(OC(C)CC(C)C)OC(C)CC(C)C)OC(C)CSP(=S)(OC(C)CC(C)C)OC(C)CC(C)C]
1
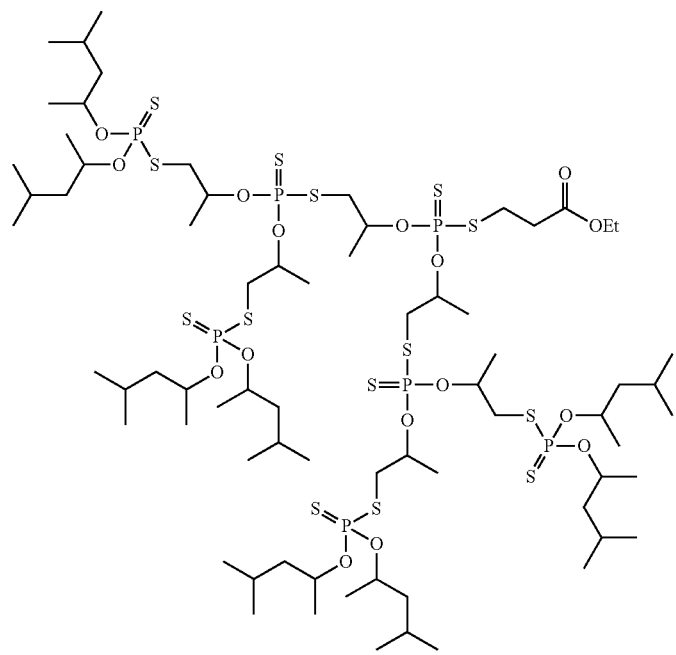
2

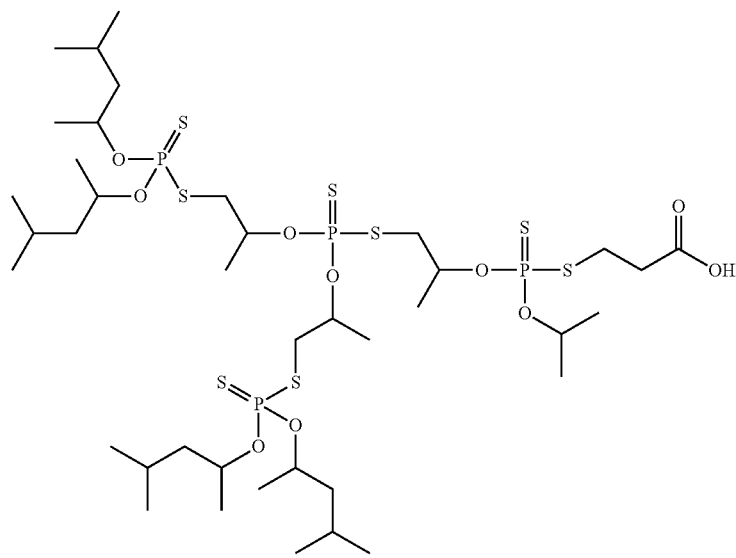 [SMILES: CC(C)CC(C)OP(=S)(OC(C)CC(C)C)SCC(C)OP(=S)(OC(C)CSP(=S)(OC(C)CC(C)C)OC(C)CC(C)C)SCC(C)OP(=S)(OC(C)C)SCCC(=O)O]
3
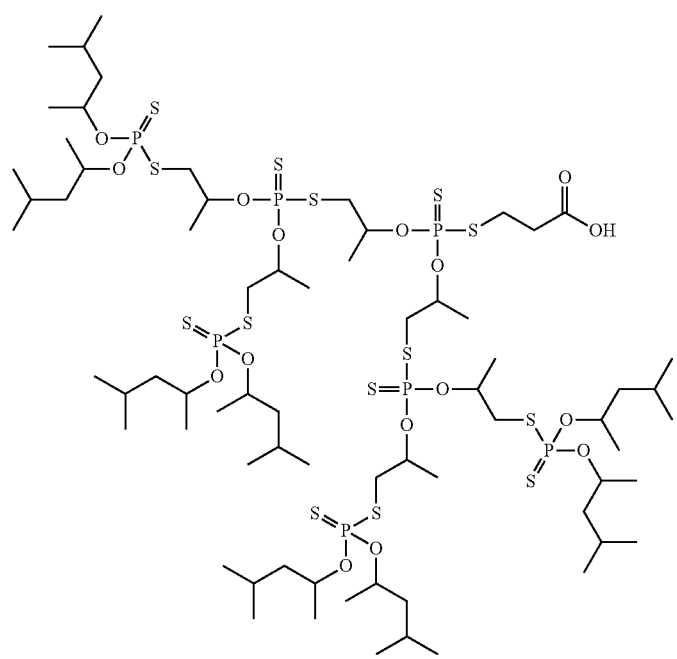 [SMILES: CC(C)CC(C)OP(=S)(OC(C)CC(C)C)SCC(C)OP(=S)(OC(C)CSP(=S)(OC(C)CC(C)C)OC(C)CC(C)C)SCC(C)OP(=S)(OC(C)CSP(=S)(OC(C)CSP(=S)(OC(C)CC(C)C)OC(C)CC(C)C)OC(C)CSP(=S)(OC(C)CC(C)C)OC(C)CC(C)C)SCCC(=O)O]
4
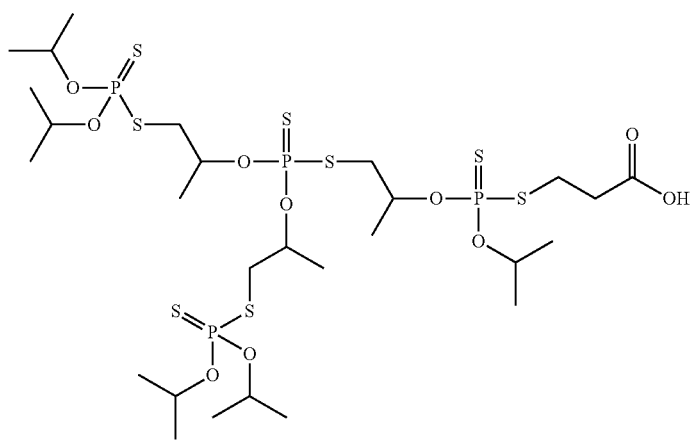 [SMILES: CC(C)OP(=S)(OC(C)C)SCC(C)OP(=S)(OC(C)CSP(=S)(OC(C)C)OC(C)C)SCC(C)OP(=S)(OC(C)C)SCCC(=O)O]
5

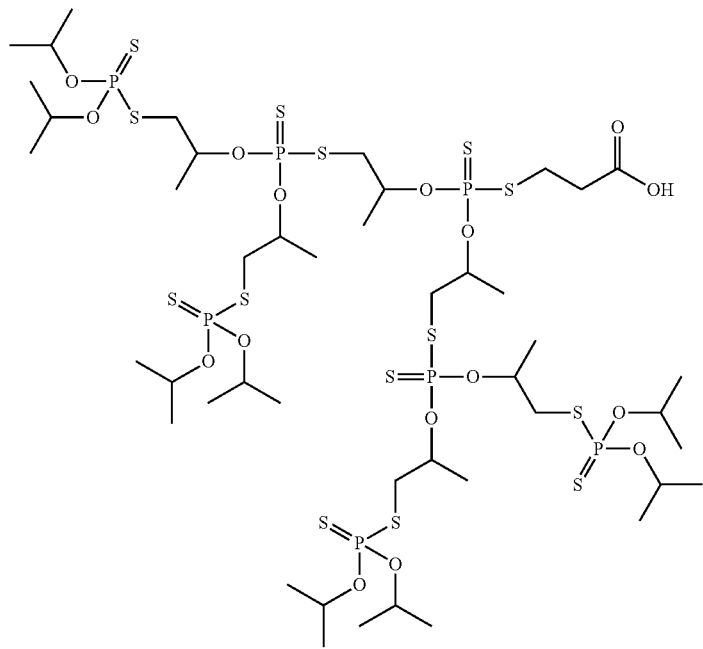 [SMILES: CC(C)OP(=S)(OC(C)C)SCC(C)OP(=S)(OC(C)CSP(=S)(OC(C)C)OC(C)C)SCC(C)OP(=S)(OC(C)CSP(=S)(OC(C)CSP(=S)(OC(C)C)OC(C)C)OC(C)CSP(=S)(OC(C)C)OC(C)C)SCCC(=O)O]
6
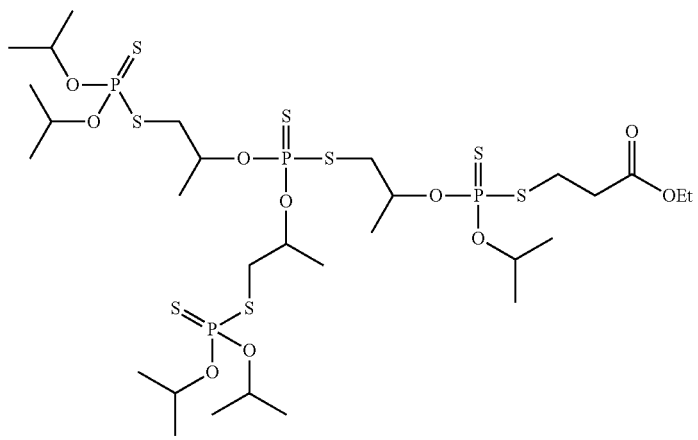 [SMILES: CCOC(=O)CCSP(=S)(OC(C)C)OC(C)CSP(=S)(OC(C)CSP(=S)(OC(C)C)OC(C)C)OC(C)CSP(=S)(OC(C)C)OC(C)C]
7

-continued
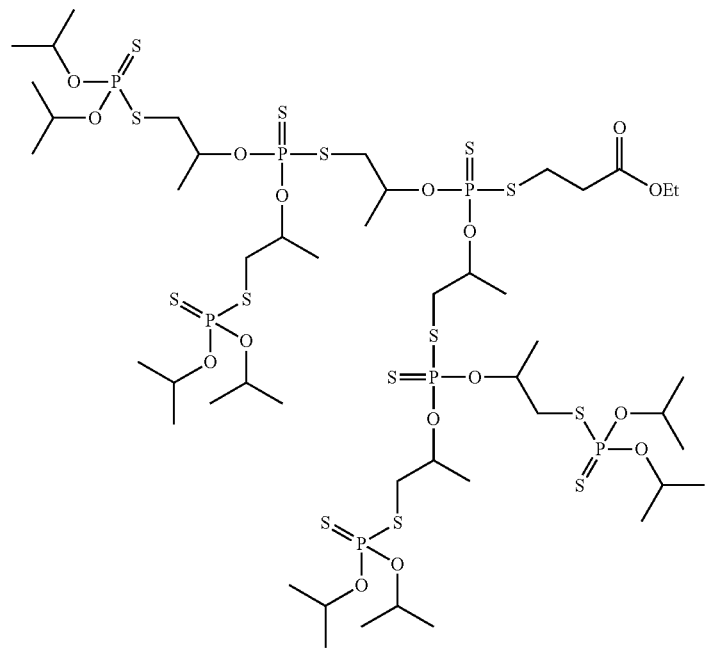 [SMILES: CCOC(=O)CCSP(=S)(OC(C)CSP(=S)(OC(C)CSP(=S)(OC(C)C)OC(C)C)OC(C)CSP(=S)(OC(C)C)OC(C)C)OC(C)CSP(=S)(OC(C)CSP(=S)(OC(C)C)OC(C)C)OC(C)CSP(=S)(OC(C)C)OC(C)C]
8
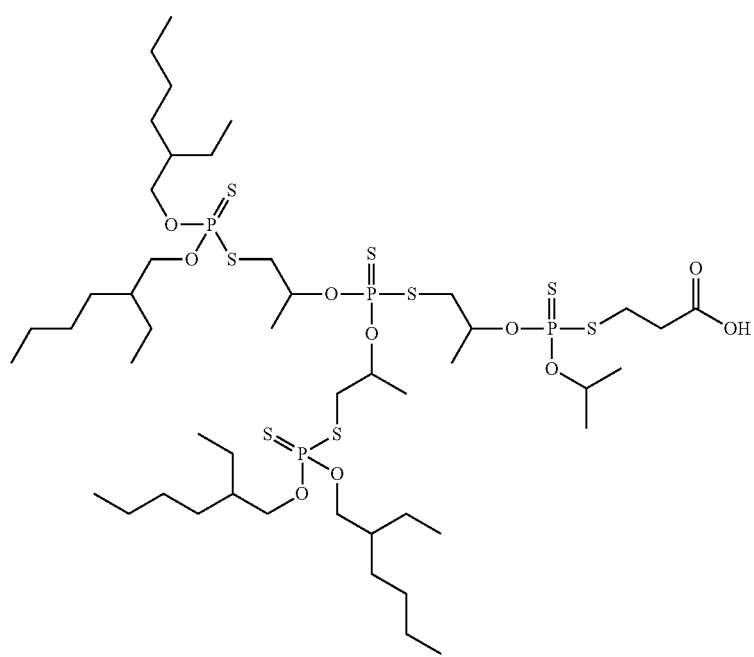 [SMILES: CCCCC(CC)COP(=S)(OCC(CC)CCCC)SCC(C)OP(=S)(OC(C)CSP(=S)(OCC(CC)CCCC)OCC(CC)CCCC)SCC(C)OP(=S)(OC(C)C)SCCC(=O)O]
9

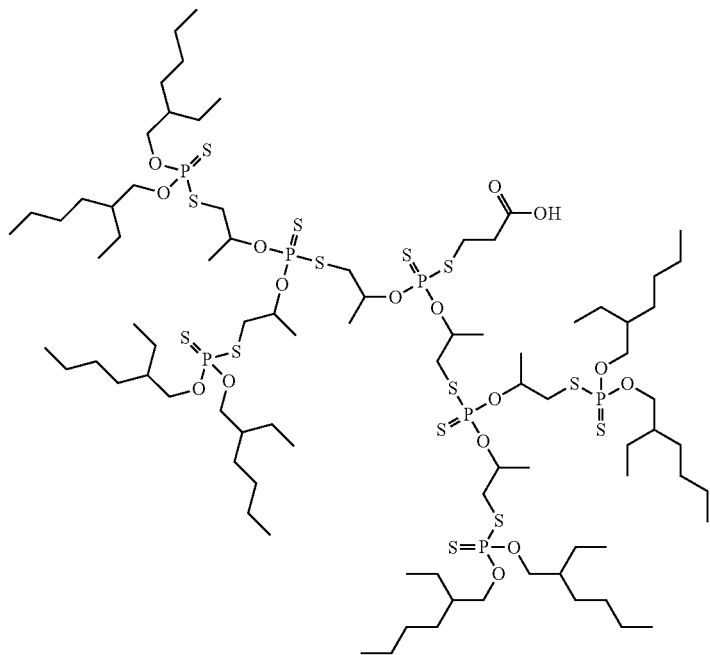
10
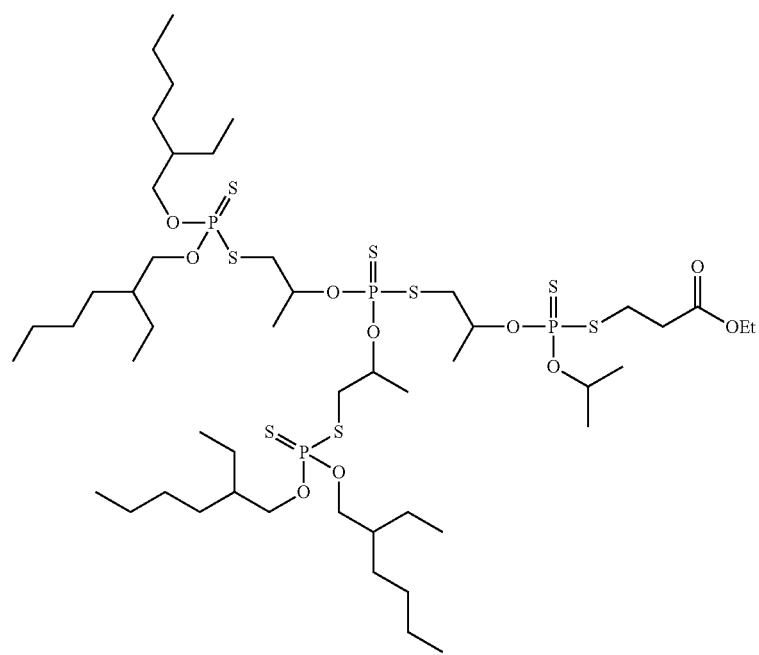 [SMILES: CCCCC(CC)COP(=S)(OCC(CC)CCCC)SCC(C)OP(=S)(OC(C)CSP(=S)(OCC(CC)CCCC)OCC(CC)CCCC)SCC(C)OP(=S)(OC(C)C)SCCC(=O)OCC]
11

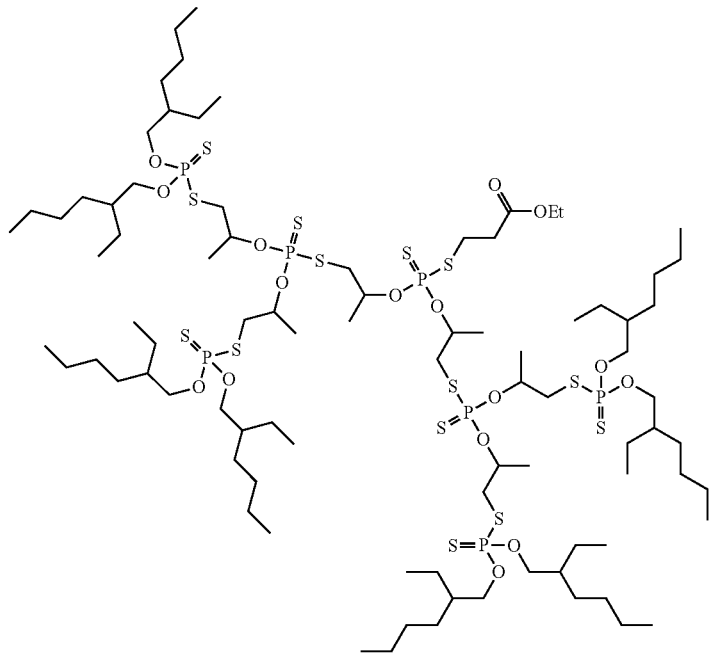 [SMILES: CCCCC(CC)COP(=S)(OCC(CC)CCCC)SCC(C)OP(=S)(OC(C)CSP(=S)(OCC(CC)CCCC)OCC(CC)CCCC)SCC(C)OP(=S)(OC(C)CSP(=S)(OC(C)CSP(=S)(OCC(CC)CCCC)OCC(CC)CCCC)OC(C)CSP(=S)(OCC(CC)CCCC)OCC(CC)CCCC)SCCC(=O)OCC]
12
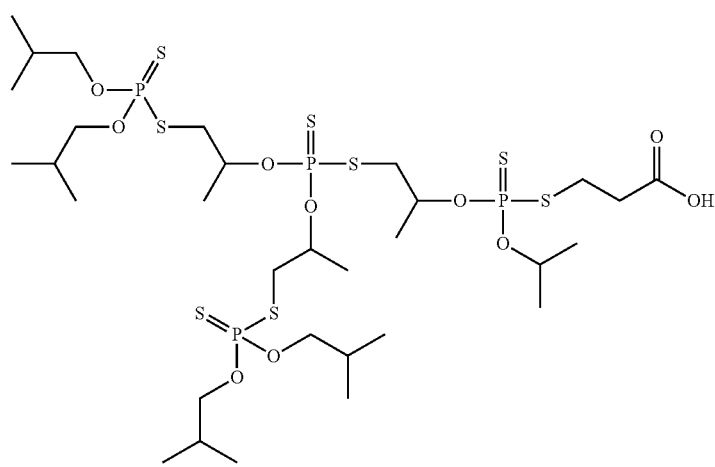
13

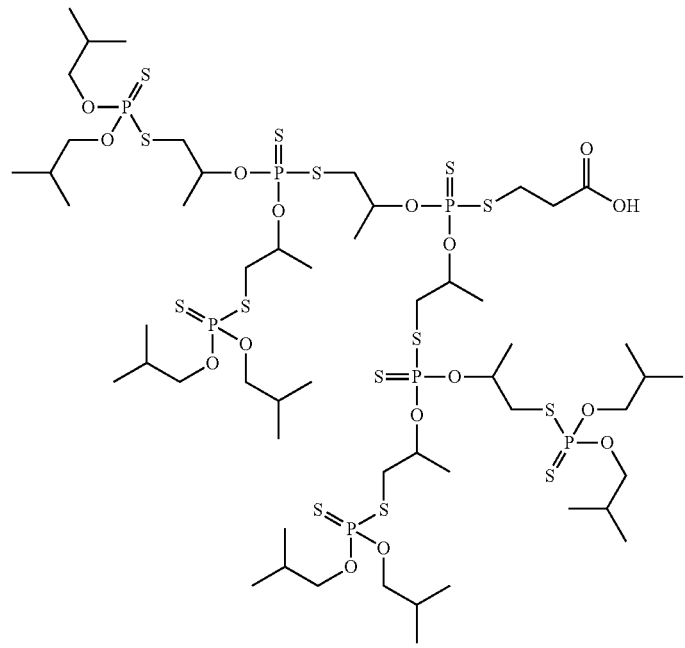 [SMILES: CC(C)COP(=S)(OCC(C)C)SCC(C)OP(=S)(OC(C)CSP(=S)(OCC(C)C)OCC(C)C)SCC(C)OP(=S)(OC(C)CSP(=S)(OC(C)CSP(=S)(OCC(C)C)OCC(C)C)OC(C)CSP(=S)(OCC(C)C)OCC(C)C)SCCC(=O)O]
14
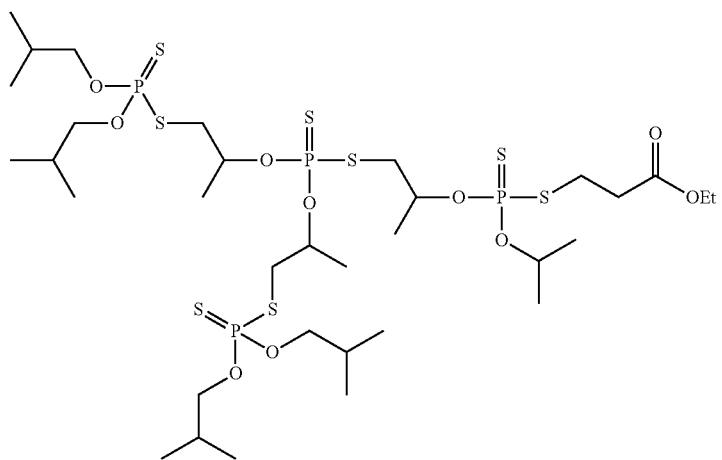 [SMILES: CCOC(=O)CCSP(=S)(OC(C)C)OC(C)CSP(=S)(OC(C)CSP(=S)(OCC(C)C)OCC(C)C)OC(C)CSP(=S)(OCC(C)C)OCC(C)C]
15

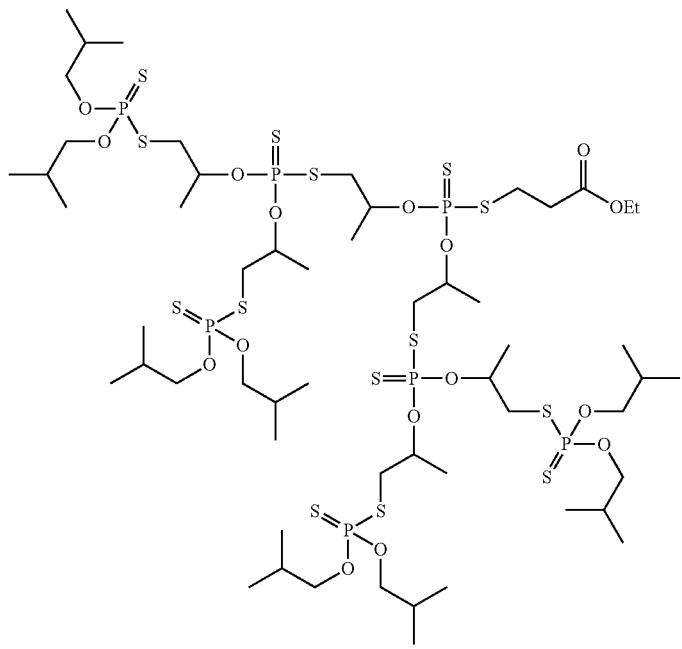
16
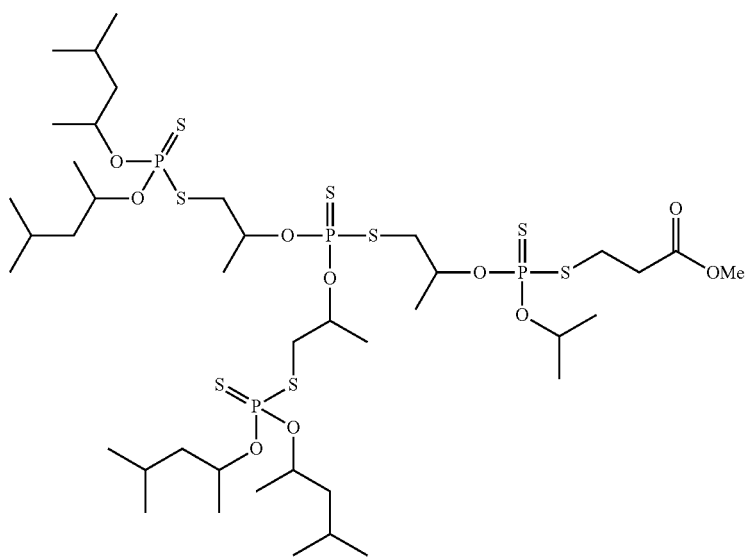 [SMILES: COC(=O)CCSP(=S)(OC(C)C)OC(C)CSP(=S)(OC(C)CSP(=S)(OC(C)CC(C)C)OC(C)CC(C)C)OC(C)CSP(=S)(OC(C)CC(C)C)OC(C)CC(C)C]
17

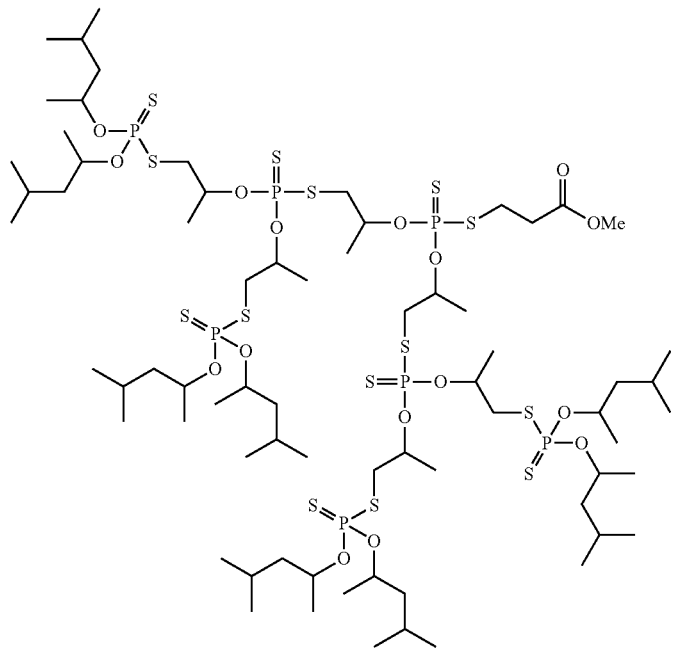
18
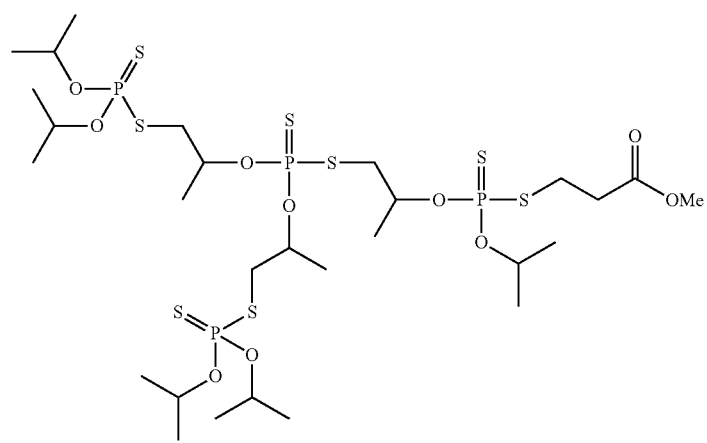 [SMILES: COC(=O)CCSP(=S)(OC(C)C)OC(C)CSP(=S)(OC(C)CSP(=S)(OC(C)C)OC(C)C)OC(C)CSP(=S)(OC(C)C)OC(C)C]
19

-continued
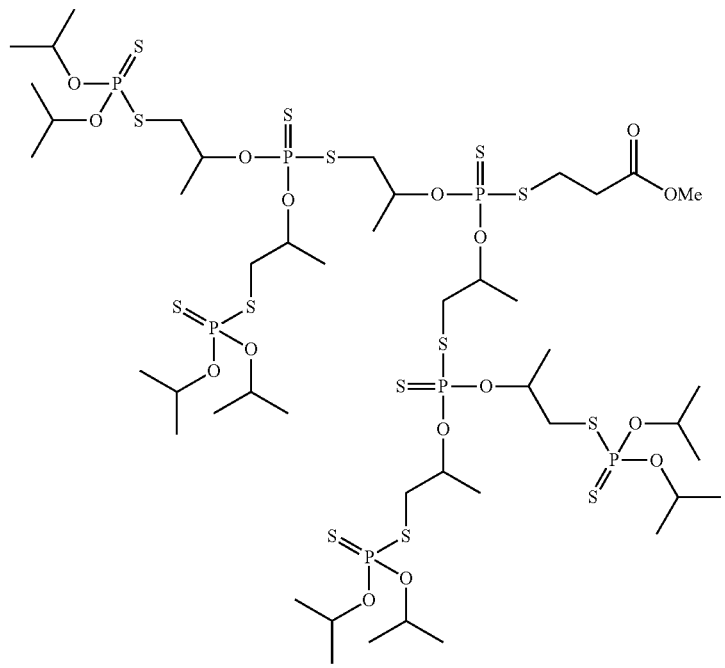
20
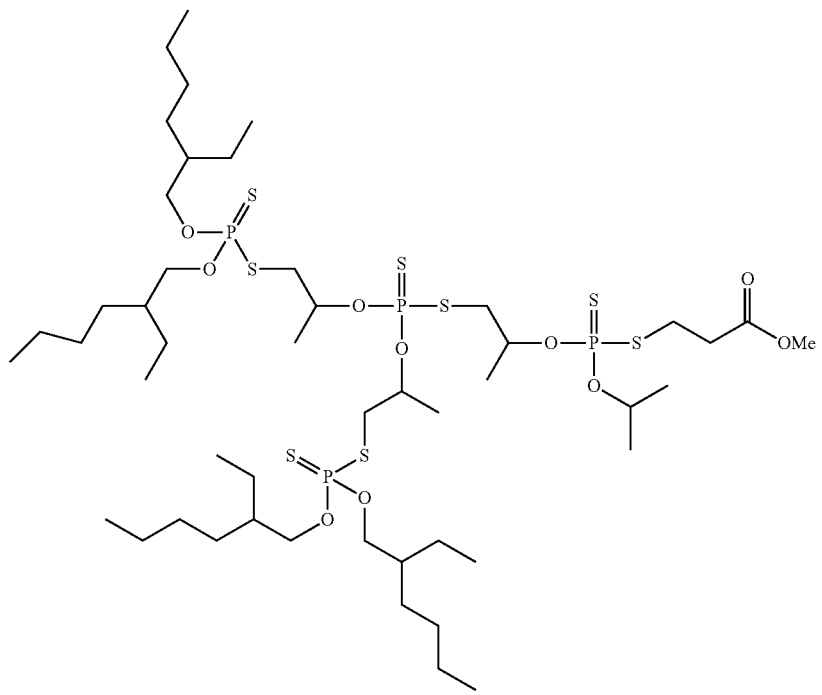 [SMILES: CCCCC(CC)COP(=S)(OCC(CC)CCCC)SCC(C)OP(=S)(OC(C)CSP(=S)(OCC(CC)CCCC)OCC(CC)CCCC)SCC(C)OP(=S)(OC(C)C)SCCC(=O)OC]
21

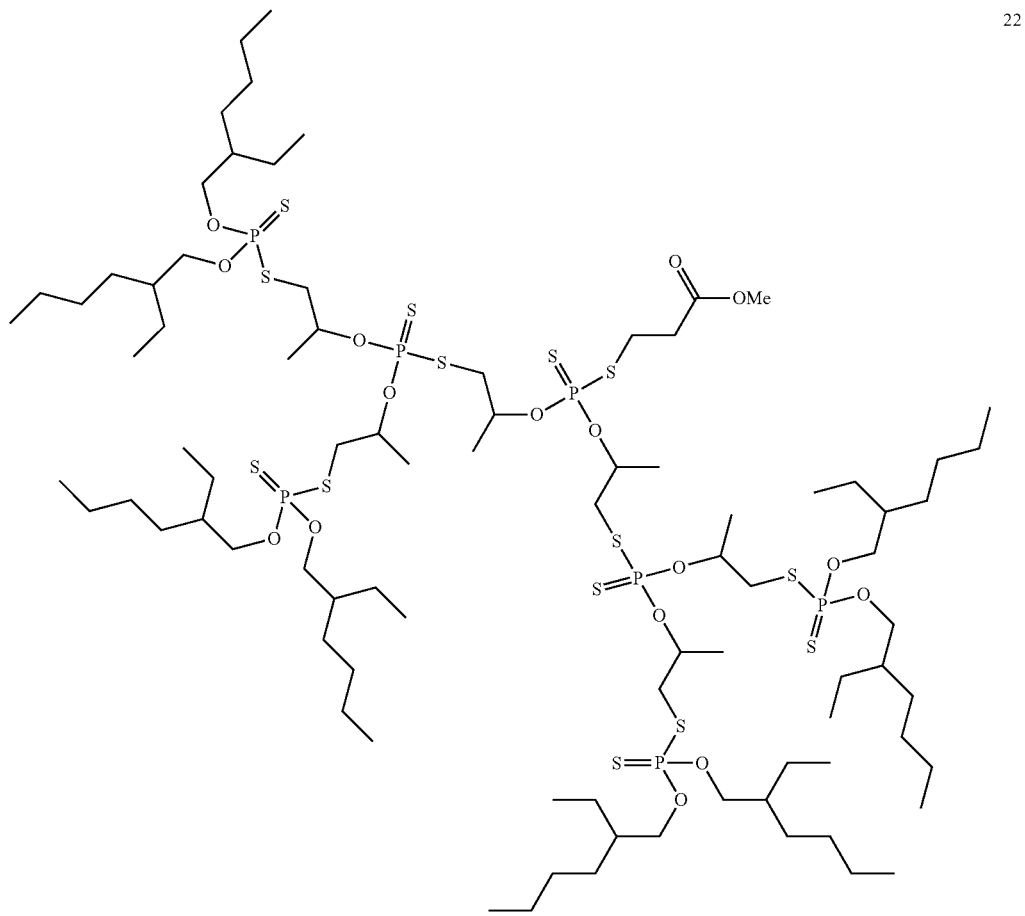
22
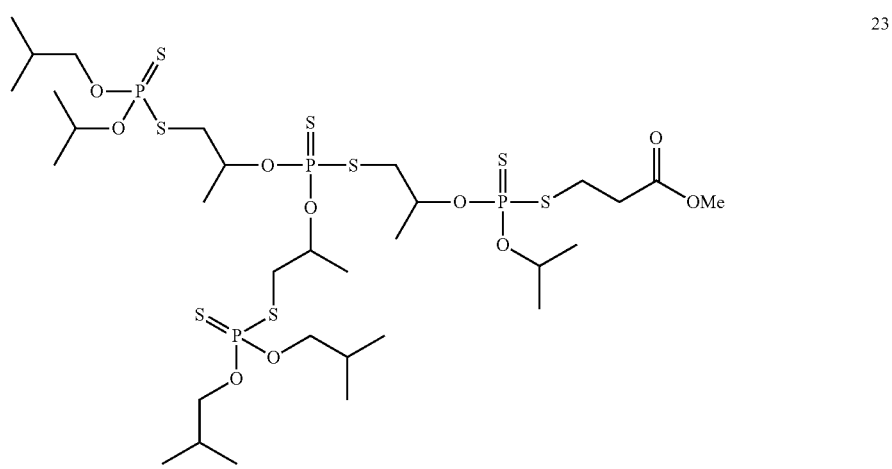
23

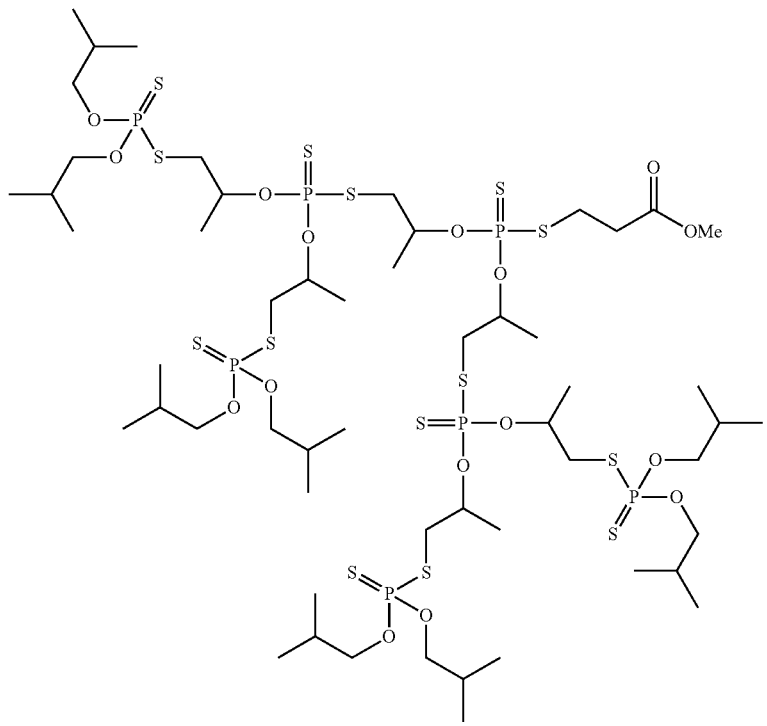

As used herein, the term "alkyl," as well as the as the alkyl moieties of other groups referred herein (e.g., alkoxyl) may be a linear or branched chain saturated hydrocarbon containing from 1 to 30 carbon atoms.

As used herein, the term "alkenyl" means a straight or branched hydrocarbon chain containing at least one carbon-carbon double bond. For example, the term "$C_2$-$C_4$ alkenyl" means an alkenyl group containing 2-4 carbon atoms. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

As used herein, the term "substituted" refers to wherein one or more hydrogen atoms are each independently replaced with a non-hydrogen substituent.

As used herein, the term "alkoxy" refers to an alkyl group attached to the parent molecular moiety through an oxygen atom.

As used herein, the term "alkenyloxy" refers to an alkenyl group attached to the parent molecular moiety through an oxygen atom.

As used herein, the term "alkoxyalkyl" refers to a group -alkylene-O-alkyl.

As used herein, the term "alkylene" refers to a methylene or polymethylene group, i.e., —(CH$_2$)$_z$—, wherein z is a positive integer from 1 to 30.

As used herein, the term "cycloalkyl" means a non-aromatic, monocyclic or polycyclic ring comprising carbon and hydrogen atoms. A cycloalkyl group can have one or more carbon-carbon double bonds in the ring so long as the ring is not rendered aromatic by their presence.

As used herein, the term "cycloalkylalkyl" means a cycloalkyl group that is attached to the parent molecular moiety with an alkylene linker group consisting of at least one carbon.

As used herein the term "hydroxyalkyl" refers to the group $R^a$-$R^b$— wherein $R^a$ is HO— and $R^b$ is alkylene.

As used herein the term "hydroxyalkyleneoxy" refers to the group $R^a$-$R^b$-$R^c$ wherein $R^a$ is HO—, $R^b$ is alkylene and $R^c$ is —O—.

As used herein, the phrase "reactive group" refers to an electrophilic chemical group that is capable of attaching a carbon atom of a substituent to a sulfur atom in a nucleophilic P—SH group, for example, in a dithiophosphate, or attaching a carbon atom of a substituent to an oxygen atom of a nucleophilic P—OH, for example, in a phosphate. Such reactive groups are readily recognized by those skilled in the art. Examples of suitable reactive groups in accordance with the present invention include alkyl halides, activated alkyl alcohols including tosylates, triflates and mesylates, epoxides, and acrylate derivatives. In certain embodiments, the reactive group can be selected from 1-bromohexadecane, methyl iodide, benzyl bromide, vinyl butyl ether, ethyl acrylate, 1,2-epoxydodecane, acrylic acid, 1,2-epoxydecane, and 2-hydroxyethyl acrylate.

As used herein, the phrase "phosphorodithioating agent" means a compound with at least one phosphorous atom and two sulfur atoms that can react with a hydroxyl group to form a phosphorodithioate of the structure:

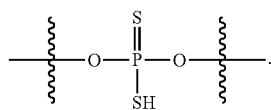 [SMILES: *OP(=S)(S)O*]

For purpose of the present invention, phosphorodithioating agents include, for example, P$_2$S$_5$ and X$_2$P(S)SH, wherein each X is independently C$_2$-C$_{30}$alkoxy or C$_2$-C$_{30}$alkenyloxy. Further examples of phosphorodithioating agents in accordance with the present invention include O',O'-diisopropyl dithiophosphoric acid, O',O'-di-ethyl dithiophosphoric acid, O',O'-di-n-propyl dithiophosphoric acid, O',O'-di-n-butyl dithiophosphoric acid, O',O'-di-isobutyl dithiophosphoric acid, O',O'-di-sec-butyl dithiophosphoric acid, O',O'-di-amyl dithiophosphoric acid and O',O'-di-hexyl dithiophosphoric acid, or mixtures thereof.

As used herein, the phrase "effective amount" means an amount sufficient to provide the desired effect. For example, the compounds of the present invention are useful as antiwear agents when incorporated into lubricant compositions. Therefore, an effective amount of a compound of the present invention when incorporated into a lubricant composition can be an amount that improves the antiwear properties of the lubricant compositions comprising a compound of the instant invention as compared to the same lubricant composition that does not comprise a compound of the instant invention.

As used herein, the terms "oil composition," "lubrication composition," "lubricating composition," "lubricating oil composition," "lubricating oil," "lubricant composition," "fully formulated lubricant composition," and "lubricant" are considered synonymous, fully interchangeable terminology referring to the finished lubrication product comprising a major amount of a base oil plus a minor amount of an additive composition.

Although many of the compounds of formula I are substantially neutral, the present invention also contemplates base addition salts of compounds of formula I. The chemical bases that may be used as reagents to prepare tribologically acceptable base salts of those compounds of formula I that are acidic in nature are those that form base salts with such compounds. Such base salts include, but are not limited to cations such as alkali metal cations (e.g., potassium and sodium) and alkaline earth metal cations (e.g., calcium and magnesium), ammonium or amine addition salts such as N-methylglucamine-(meglumine), and alkanolammonium and other base salts of tribologically acceptable organic amines, including but not limited to alkylamines such as octylamine and oleylamine.

The phrase "tribologically acceptable salt(s)", as used herein, unless otherwise indicated, includes salts of acidic or basic groups which may be present in the compounds of the present disclosure. The compounds of the present disclosure that are basic in nature are capable of forming a wide variety of salts with various inorganic and organic acids. The acids that may be used to prepare tribologically acceptable acid addition salts of such basic compounds are those that form acid addition salts, i.e., salts containing tribologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present disclosure that include a basic moiety, such as an amino group, may form tribologically acceptable salts with various amines, in addition to the acids mentioned above.

The compounds of the present disclosure include all stereoisomers (e.g., cis and trans isomers) and all optical isomers of compounds of Formula I (e.g., R and S enantiomers), certain positional isomers, as well as racemic, diastereomeric and other mixtures of such isomers. Those skilled in the relevant art can readily envision such isomers and the isomers are included within the scope of the present invention.

The compounds and salts of the present disclosure can exist in several tautomeric forms, including the enol and imine form, and the keto and enamine form and geometric isomers and mixtures thereof. All such tautomeric forms are included within the scope of the present disclosure. Even though one tautomer may be described, the present disclosure includes all tautomers of the present compounds.

One aspect of the present invention is a compound prepared by a process comprising:
  a. reacting a phosphorodithioate with a first epoxide;
  b. reacting the product of step a) with a first phosphorodithioating agent;
  c. reacting the product of step b) with a second epoxide;
  d. reacting the product of step c) with a second phosphorodithioating agent; and
  e. reacting the product of step d) with a reactive group.

In certain embodiments, the first and second phosphorodithioating agents are each independently selected from the group consisting of $P_2S_5$ and $X_2P(S)SH$, wherein each X is independently $C_2$-$C_{30}$alkoxy or $C_2$-$C_{30}$alkenyloxy. In another embodiment, $X_2P(S)SH$ is O',O'-dialkyl dithiophosphoric acid. In certain embodiments, the O',O'-dialkyl dithiophosphoric acid is selected from the group consisting of O',O'-diisopropyl dithiophosphoric acid, O',O'-di-ethyl dithiophosphoric acid, O',O'-di-n-propyl dithiophosphoric acid, O',O'-di-n-butyl dithiophosphoric acid, O',O'-di-isobutyl dithiophosphoric acid, O',O'-di-sec-butyl dithiophosphoric acid, O',O'-di-amyl dithiophosphoric acid and O',O'-di-hexyl dithiophosphoric acid, or mixtures thereof.

In one embodiment, the first epoxide and the second epoxide are the same or different. In another embodiment, the first and second epoxide are each independently selected from ethylene oxide and propylene oxide.

The compounds of the present invention are contemplated to be used as an additive in lubricating base oil. As used herein, the term "base oil" refers to oils categorized by the American Petroleum Institute (API) category groups Group I-V oils as well as animal oils, vegetable oils (e.g. castor oil and lard oil), petroleum oils, mineral oils, synthetic oils, and oils derived from coal or shale. The American Petroleum Institute has categorized these different basestock types as follows: Group I, greater than 0.03 wt percent sulfur, and/or less than 90 vol percent saturates, viscosity index between 80 and 120; Group II, less than or equal to 0.03 wt percent sulfur, and greater than or equal to 90 vol percent saturates, viscosity index between 80 and 120; Group III, less than or equal to 0.03 wt percent sulfur, and greater than or equal to 90 vol percent saturates, viscosity index greater than 120; Group IV, all polyalphaolefins. Hydrotreated basestocks and catalytically dewaxed basestocks, because of their low sulfur and aromatics content, generally fall into the Group II and Group III categories. Polyalphaolefins (Group IV basestocks) are synthetic base oils prepared from various alpha olefins and are substantially free of sulfur and aromatics.

Groups I, II, and III are mineral oil process stocks. Group IV base oils contain true synthetic molecular species, which are produced by polymerization of olefinically unsaturated hydrocarbons. Many Group V base oils are also true synthetic products and may include diesters, polyol esters, polyalkylene glycols, alkylated aromatics, polyphosphate esters, polyvinyl ethers, and/or polyphenyl ethers, and the like, but may also be naturally occurring oils, such as vegetable oils. It should be noted that although Group III base oils are derived from mineral oil, the rigorous processing that these fluids undergo causes their physical properties to be very similar to some true synthetics, such as PAOs. Therefore, oils derived from Group III base oils may sometimes be referred to as synthetic fluids in the industry.

The compounds of the present invention can be added to base oils in the form of a mineral oil or synthetic oil, animal oil, vegetable oil, or mixtures thereof. In general, the mineral oils, both paraffinic and naphthenic and mixtures thereof can be employed as lubricating oil or as the grease vehicle. Also contemplated are greases in which any of the foregoing oils are employed as a base.

The compound of the present invention, in addition to other additive components, can be added to a lubricating oil to form a finished fluid having a viscosity of at least an SAE 90 or 75W-85. Viscosity indexes from about 95 to 130 being preferred. The average molecular weights of these oils can range from about 250 to about 800.

Where the lubricant is employed as a grease, the lubricant is generally used in an amount sufficient to balance the total grease composition, after accounting for the desired quantity of the thickening agent, and other additive components included in the grease formulation. A wide variety of materials can be employed as thickening or gelling agents. These can include any of the conventional metal salts or soaps, such as calcium, or lithium stearates or hydroxystearates, which are dispersed in the lubricating vehicle in grease-forming quantities in an amount sufficient to impart to the resulting grease composition the desired consistency. Other thickening agents that can be employed in the grease formulation comprise the non-soap thickeners, such as surface-modified clays and silicas, aryl ureas, calcium complexes and similar materials. In general, grease thickeners can be employed which do not melt or dissolve when used at the required temperature within a particular environment; however, in all other respects, any material which is normally employed for thickening or gelling hydrocarbon fluids for forming greases can be used in the present invention.

Where synthetic oils, or synthetic oils employed as the vehicle for the grease, are desired in preference to mineral oils, or in mixtures of mineral and synthetic oils, various synthetic oils may be used. Typical synthetic oils include polyisobutylenes, polybutenes, polydecenes, siloxanes and silicones (polysiloxanes).

The present invention provides lubricant compositions comprising a major amount of oil of lubricating viscosity or a grease prepared therefrom and a minor amount of a compound of the present invention. The compound of the present invention can be in the lubricant composition in an amount between about 0.001% to 10%, between 0.01% to 5%, between 0.01% to 1.0%, between 0.5% to 2.0%, and between 0.015% to about 0.5% by weight of the total composition. In some embodiments, lubricating compositions can contain between about from 0.01% to 0.5%, between about 0.01 and about 0.4 wt %, or between about 0.01 and about 0.3 wt %, or between about 0.01 and about 0.2 wt %.

As mentioned above, the compounds of the present invention can be readily formulated into lubricant compositions suitable for use with a variety of machine parts and components. The lubricant compositions comprising a compound of the present invention can optionally further comprise one or more other additive components such that the lubricant compositions. The list of additive components disclosed below is not exhaustive and additive components not expressly disclosed herein are well known to the skilled artisan and may also be included in the lubricant compositions. Without limitation, additive components that can be used in the lubricant compositions of the present invention include antioxidants, additional antiwear agents, corrosion inhibitors, detergents, extreme pressure agents, viscosity index improvers, and friction reducers.

In one embodiment, the lubricant composition of the present invention comprises a compound of The present invention and at least one additional additive composition selected from the group consisting of an antioxidant, antiwear agents, corrosion inhibitor, detergent, extreme pressure agent, dispersant, viscosity index improvers, and friction modifiers.

The compounds of the present invention can be incorporated into an oil of lubricating viscosity directly. Alternatively, compounds of the present invention can be prepared in combination with other lubricant additives to form a lubricant additive composition. Generally, the lubricant additive composition will further be incorporated into the oil of lubricating viscosity at a particular wt % of the lubricant additive package relative to the total weight of the final lubricant composition. The wt % selected is generally referred to as the treat rate and the lubricant composition containing the lubricant additive composition is generally referred to as a finished fluid.

In one embodiment the present invention provides a lubricant additive composition comprising a compound of the present invention and at least one additional additive component. The one or more additional additive component(s) can be selected from an antioxidant, antiwear agents, corrosion inhibitor, detergent, extreme pressure agent, viscosity index improvers, and friction modifiers.

Antioxidants

Antioxidant compounds are known and include, for example, phenates, phenate sulfides, sulfurized olefins, phosphosulfurized terpenes, sulfurized esters, aromatic amines, alkylated diphenylamines (e.g., nonyl diphenylamine, di-nonyl diphenylamine, octyl diphenylamine, di-octyl diphenylamine), phenyl-alpha-naphthylamines, alkylated phenyl-alpha-naphthylamines, hindered non-aromatic amines, phenols, hindered phenols, oil-soluble molybdenum compounds, macromolecular antioxidants, or mixtures thereof. A single antioxidant or a combination of two or more can be used.

The hindered phenol antioxidant may contain a secondary butyl and/or a tertiary butyl group as a sterically hindering group. The phenol group may be further substituted with a hydrocarbyl group and/or a bridging group linking to a second aromatic group. Examples of suitable hindered phenol antioxidants include 2,6-di-tert-butylphenol, 4-methyl-2,6-di-tert-butylphenol, 4-ethyl-2,6-di-tert-butylphenol, 4-propyl-2,6-di-tert-butylphenol or 4-butyl-2,6-di-tert-butylphenol, or 4-dodecyl-2,6-di-tert-butylphenol. In an embodiment the hindered phenol antioxidant may be an ester and may include, e.g., an addition product derived from 2,6-di-tert-butylphenol and an alkyl acrylate, wherein the alkyl group may contain about 1 to about 18, or about 2 to about 12, or about 2 to about 8, or about 2 to about 6, or about 4 carbon atoms.

Useful antioxidants may include diarylamines and high molecular weight phenols. In an embodiment, the lubricating oil composition may contain a mixture of a diarylamine and a high molecular weight phenol, such that each antioxidant may be present in an amount sufficient to provide up to about 5%, by weight of the antioxidant, based upon the final weight of the lubricating oil composition. In some embodiments, the antioxidant may be a mixture of about 0.3 to about 1.5% diarylamine and about 0.4 to about 2.5% high molecular weight phenol, by weight, based upon the final weight of the lubricating oil composition.

Examples of suitable olefins that may be sulfurized to form a sulfurized olefin include propylene, butylene, isobutylene, polyisobutylene, pentene, hexene, heptene, octene, nonene, decene, undecene, dodecene, tridecene, tetradecene, pentadecene, hexadecene, heptadecene, octadecene, nonadecene, eicosene or mixtures thereof. In an embodiment, hexadecene, heptadecene, octadecene, nonadecene, eicosene or mixtures thereof and their dimers, trimers and tetramers are especially useful olefins. Alternatively, the olefin may be a Diels-Alder adduct of a diene such as 1,3-butadiene and an unsaturated ester, such as, butylacrylate.

Another class of sulfurized olefin includes sulfurized fatty acids and their esters. The fatty acids are often obtained from vegetable oil or animal oil and typically contain about 4 to about 22 carbon atoms. Examples of suitable fatty acids and their esters include triglycerides, oleic acid, linoleic acid, palmitoleic acid or mixtures thereof. Often, the fatty acids are obtained from lard oil, tall oil, peanut oil, soybean oil, cottonseed oil, sunflower seed oil or mixtures thereof. Fatty acids and/or ester may be mixed with olefins, such as α-olefins.

The one or more antioxidant(s) may be present in ranges of from about 0 wt. % to about 20 wt. %, or about 0.1 wt. % to about 10 wt. %, or about 1 wt. % to about 5 wt. %, of the lubricating composition.

Antiwear Agents

Examples of additional suitable antiwear agents include, but are not limited to, a metal thiophosphate; a metal dialkyldithiophosphate; a phosphoric acid ester or salt thereof; a phosphate ester(s); a phosphite; a phosphorus-containing carboxylic ester, ether, or amide; a sulfurized olefin; thiocarbamate-containing compounds including, thiocarbamate esters, alkylene-coupled thiocarbamates, and bis(S-alkyldithiocarbamyl)disulfides; and mixtures thereof. The phosphorus containing antiwear agents are more fully described in European Patent No. 0612 839. The metal in the dialkyl dithio phosphate salts may be an alkali metal, alkaline earth metal, aluminum, lead, tin, molybdenum, manganese, nickel, copper, titanium, or zinc. A useful antiwear agent may be a zinc dialkyldithiophosphate.

The antiwear agent may be present in ranges of from about 0 wt. % to about 15 wt. %, or about 0.01 wt. % to about 10 wt. %, or about 0.05 wt. % to about 5 wt. %, or about 0.1 wt. % to about 3 wt. % of the total weight of the lubricating composition.

Detergents

The lubricant composition may optionally comprise one or more neutral, low based, or overbased detergents, and mixtures thereof. Suitable detergent substrates include phenates, sulfur containing phenates, sulfonates, calixarates, salixarates, salicylates, carboxylic acids, phosphorus acids, mono- and/or di-thiophosphoric acids, alkyl phenols, sulfur coupled alkyl phenol compounds and methylene bridged phenols. Suitable detergents and their methods of preparation are described in greater detail in numerous patent publications, including U.S. Pat. No. 7,732,390, and references cited therein.

The detergent substrate may be salted with an alkali or alkaline earth metal such as, but not limited to, calcium, magnesium, potassium, sodium, lithium, barium, or mixtures thereof. In some embodiments, the detergent is free of barium. A suitable detergent may include alkali or alkaline earth metal salts of petroleum sulfonic acids and long chain mono- or di-alkylarylsulfonic acids with the aryl group being one of benzyl, tolyl, and xylyl.

Overbased detergent additives are well known in the art and may be alkali or alkaline earth metal overbased detergent additives. Such detergent additives may be prepared by reacting a metal oxide or metal hydroxide with a substrate and carbon dioxide gas. The substrate is typically an acid, for example, an acid such as an aliphatic substituted sulfonic acid, an aliphatic substituted carboxylic acid, or an aliphatic substituted phenol.

The terminology "overbased" relates to metal salts, such as metal salts of sulfonates, carboxylates, and phenates, wherein the amount of metal present exceeds the stoichiometric amount. Such salts may have a conversion level in excess of 100% (i.e., they may comprise more than 100% of the theoretical amount of metal needed to convert the acid to its "normal," "neutral" salt). The expression "metal ratio," often abbreviated as MR, is used to designate the ratio of total chemical equivalents of metal in the overbased salt to chemical equivalents of the metal in a neutral salt according to known chemical reactivity and stoichiometry. In a normal or neutral salt, the metal ratio is one and in an overbased salt, the MR, is greater than one. Such salts are commonly referred to as overbased, hyperbased, or superbased salts and may be salts of organic sulfur acids, carboxylic acids, or phenols.

The overbased detergent may have a metal ratio of from 1.1:1, or from 2:1, or from 4:1, or from 5:1, or from 7:1, or from 10:1.

In some embodiments, a detergent can be used for reducing or preventing rust in a gear, axle, or engine.

The detergent may be present at about 0 wt. % to about 10 wt. %, or about 0.1 wt. % to about 8 wt. %, or about 1 wt. % to about 4 wt. %, or greater than about 4 wt. % to about 8 wt. % based on the total weight of the lubricant composition.

Dispersants

The lubricant composition may optionally further comprise one or more dispersants or mixtures thereof. Dispersants are often known as ashless-type dispersants because, prior to mixing in a lubricating oil composition, they do not contain ash-forming metals and they do not normally contribute any ash when added to a lubricant. Ashless-type dispersants are characterized by a polar group attached to a relatively high molecular or weight hydrocarbon chain. Typical ashless dispersants include N-substituted long chain alkenyl succinimides. Examples of N-substituted long chain alkenyl succinimides include polyisobutylene succinimide with number average molecular weight of the polyisobutylene substituent in a range of about 350 to about 5000, or about 500 to about 3000. Succinimide dispersants and their preparation are disclosed, for instance in U.S. Pat. No. 7,897,696 and U.S. Pat. No. 4,234,435. Succinimide dispersants are typically an imide formed from a polyamine, typically a poly(ethyleneamine).

In some embodiments the lubricant composition comprises at least one polyisobutylene succinimide dispersant derived from polyisobutylene with number average molecular weight in the range about 350 to about 5000, or about 500 to about 3000. The polyisobutylene succinimide may be used alone or in combination with other dispersants.

In some embodiments, polyisobutylene (PIB), when included, may have greater than 50 mol %, greater than 60 mol %, greater than 70 mol %, greater than 80 mol %, or greater than 90 mol % content of terminal double bonds. Such a PIB is also referred to as highly reactive PIB ("HR-PIB"). HR-PIB having a number average molecular weight ranging from about 800 to about 5000 is suitable for use in embodiments of the present disclosure. Conventional non-highly reactive PIB typically has less than 50 mol %, less than 40 mol %, less than 30 mol %, less than 20 mol %, or less than 10 mol % content of terminal double bonds.

An HR-PIB having a number average molecular weight ranging from about 900 to about 3000 may be suitable. Such an HR-PIB is commercially available, or can be synthesized by the polymerization of isobutene in the presence of a non-chlorinated catalyst such as boron trifluoride, as described in U.S. Pat. No. 4,152,499 and U.S. Pat. No. 5,739,355. When used in the aforementioned thermal ene reaction, HR-PIB may lead to higher conversion rates in the reaction, as well as lower amounts of sediment formation, due to increased reactivity.

One class of suitable dispersants may be Mannich bases. Mannich bases are materials that are formed by the condensation of a higher molecular weight, alkyl substituted phenol, a polyalkylene polyamine, and an aldehyde such as formaldehyde. Mannich bases are described in more detail in U.S. Pat. No. 3,634,515.

A suitable class of dispersants may be high molecular weight esters or half ester amides.

The dispersants may also be post-treated by conventional methods by reaction with any of a variety of agents. Among these agents are boron, urea, thiourea, dimercaptothiadiazoles, carbon disulfide, aldehydes, ketones, carboxylic acids, hydrocarbon-substituted succinic anhydrides, maleic anhydride, nitriles, epoxides, carbonates, cyclic carbonates, hindered phenolic esters, and phosphorus compounds. U.S. Pat. No. 7,645,726; U.S. Pat. No. 7,214,649; and U.S. Pat. No. 8,048,831 describe some suitable post-treatment methods and post-treated products.

The dispersant, if present, can be used in an amount sufficient to provide up to about 20 wt. %, based upon the total weight of the lubricating oil composition. The amount of the dispersant that can be used may be about 0.1 wt. % to about 15 wt. %, or about 0.1 wt. % to about 10 wt. %, or about 3 wt. % to about 10 wt. %, or about 1 wt. % to about 6 wt. %, or about 7 wt. % to about 12 wt. %, based upon the total weight of the lubricating oil composition. In an embodiment, the lubricating oil composition utilizes a mixed dispersant system.

Extreme Pressure Agents

The lubricating oil compositions herein also may optionally contain one or more extreme pressure agents. Extreme Pressure (EP) agents that are soluble in the oil include sulfur- and chlorosulfur-containing EP agents, chlorinated hydrocarbon EP agents and phosphorus EP agents. Examples of such EP agents include chlorinated waxes; organic sulfides and polysulfides such as dibenzyldisulfide, bis(chlorobenzyl) disulfide, dibutyl tetrasulfide, sulfurized methyl ester of oleic acid, sulfurized alkylphenol, sulfurized dipentene, sulfurized terpene, and sulfurized Diels-Alder adducts; phosphosulfurized hydrocarbons such as the reaction product of phosphorus sulfide with turpentine or methyl oleate; phosphorus esters such as the dihydrocarbyl and trihydrocarbyl phosphites, e.g., dibutyl phosphite, diheptyl phosphite, dicyclohexyl phosphite, pentylphenyl phosphite; dipentylphenyl phosphite, tridecyl phosphite, distearyl phosphite and polypropylene substituted phenyl phosphite; metal thiocarbamates such as zinc dioctyldithiocarbamate and barium heptylphenol diacid; amine salts of alkyl and dialkylphosphoric acids, including, for example, the amine salt of the reaction product of a dialkyldithiophosphoric acid with propylene oxide; and mixtures thereof.

Friction Modifiers

The lubricating oil compositions herein may also optionally contain one or more additional friction modifiers. Suitable friction modifiers may comprise metal containing and metal-free friction modifiers and may include, but are not limited to, imidazolines, amides, amines, succinimides, alkoxylated amines, alkoxylated ether amines, amine oxides, amidoamines, nitriles, betaines, quaternary amines, imines, amine salts, amino guanidines, alkanolamides, phosphonates, metal-containing compounds, glycerol esters, sulfurized fatty compounds and olefins, sunflower oil and other naturally occurring plant or animal oils, dicarboxylic acid esters, esters or partial esters of a polyol and one or more aliphatic or aromatic carboxylic acids, and the like.

Suitable friction modifiers may contain hydrocarbyl groups that are selected from straight chain, branched chain, or aromatic hydrocarbyl groups or mixtures thereof, and may be saturated or unsaturated. The hydrocarbyl groups may be composed of carbon and hydrogen or hetero atoms such as sulfur or oxygen. The hydrocarbyl groups may range from about 12 to about 25 carbon atoms. In a embodiments the friction modifier may be a long chain fatty acid ester. In an embodiment the long chain fatty acid ester may be a mono-ester, or a di-ester, or a (tri)glyceride. The friction modifier may be a long chain fatty amide, a long chain fatty ester, a long chain fatty epoxide derivative, or a long chain imidazoline.

Other suitable friction modifiers may include organic, ashless (metal-free), nitrogen-free organic friction modifiers. Such friction modifiers may include esters formed by reacting carboxylic acids and anhydrides with alkanols and generally include a polar terminal group (e.g. carboxyl or hydroxyl) covalently bonded to an oleophilic hydrocarbon chain. An example of an organic ashless nitrogen-free friction modifier is known generally as glycerol monooleate (GMO) which may contain mono-, di-, and tri-esters of oleic acid. Other suitable friction modifiers are described in U.S. Pat. No. 6,723,685.

Aminic friction modifiers may include amines or polyamines. Such compounds can have hydrocarbyl groups that are linear, either saturated or unsaturated, or a mixture thereof and may contain from about 12 to about 25 carbon atoms. Further examples of suitable friction modifiers include alkoxylated amines and alkoxylated ether amines. Such compounds may have hydrocarbyl groups that are linear, either saturated, unsaturated, or a mixture thereof. They may contain from about 12 to about 25 carbon atoms. Examples include ethoxylated amines and ethoxylated ether amines.

The amines and amides may be used as such or in the form of an adduct or reaction product with a boron compound such as a boric oxide, boron halide, metaborate, boric acid or a mono-, di- or tri-alkyl borate. Other suitable friction modifiers are described in U.S. Pat. No. 6,300,291.

A friction modifier may be present in amounts of about 0 wt. % to about 10 wt. %, or about 0.01 wt. % to about 8 wt. %, or about 0.1 wt. % to about 4 wt. %, based on the total weight of the lubricant composition.

Viscosity Index Improvers

The lubricating oil compositions herein also may optionally contain one or more viscosity index improvers. Suitable viscosity index improvers may include polyolefins, olefin copolymers, ethylene/propylene copolymers, polyisobutenes, hydrogenated styrene-isoprene polymers, styrene/maleic ester copolymers, hydrogenated styrene/butadiene copolymers, hydrogenated isoprene polymers, alpha-olefin maleic anhydride copolymers, polymethacrylates, polyacrylates, polyalkyl styrenes, hydrogenated alkenyl aryl conjugated diene copolymers, or mixtures thereof. Viscosity index improvers may include star polymers and suitable examples are described in US Publication No. 2012/0101017 A1.

The lubricating oil compositions herein also may optionally contain one or more dispersant viscosity index improvers in addition to a viscosity index improver or in lieu of a viscosity index improver. Suitable dispersant viscosity index improvers may include functionalized polyolefins, for example, ethylene-propylene copolymers that have been functionalized with the reaction product of an acylating agent (such as maleic anhydride) and an amine; polymethacrylates functionalized with an amine, or esterified maleic anhydride-styrene copolymers reacted with an amine.

The total amount of viscosity index improver and/or dispersant viscosity index improver may be about 0 wt. % to about 20 wt. %, about 0.1 wt. % to about 15 wt. %, about 0.1 wt. % to about 12 wt. %, or about 0.5 wt. % to about 10 wt. % based on the total weight, of the lubricating composition.

Effective amounts of the various additive components for a specific formulation may be readily ascertained, but for illustrative purposes these general guides for representative effective amounts are provided. The amounts below are given in weight % of the finished fluid.

| Component | Example Ranges (wt %) | Example Ranges (wt %) |
|---|---|---|
| A compound of the present invention | 0-10 | 0.3-5 |
| Dispersant | 0-20 | 0.5-8 |
| Extreme Pressure Agent | 0-5 | 2-4 |
| Rust Inhibitor | 0-1.0 | 0.05-1.0 |
| Corrosion Inhibitor | 0-5 | 0.05-3 |
| Demulsifier | 0-5 | 0.005-1.0 |
| Antifoam Agent | 0-0.5 | 0.001-0.1 |
| Diluent | 0-10 | 1.0-5.0 |
| Lubricating Base Oil | Balance | Balance |

The compounds of the present invention, and lubricant additive compositions comprising the same, can be used in automotive gear or axle oils. Typical of such oils are automotive spiral-bevel and worm-gear axle oils which operate under extreme pressures, load and temperature conditions, hypoid gear oils operating under both high speed, low-torque and low-speed, high torque conditions.

Industrial lubrication applications in which the compounds of the present invention, and lubricant additive compositions comprising the same, can be used include hydraulic oils, industrial gear oils, slideway machines oils, circulation oils and steam turbine oils, gas turbine oils, for heavy-duty gas turbines and aircraft gas turbines, way lubricants, gear oils, compressor oils, mist oils and machine tool lubricants. Engine oils are also contemplated such as passenger car motor oils, heavy duty diesel engine oils, marine engine oils, locomotives, and high speed automotive diesel engines.

Functional fluids can also be prepared from the compounds of the present invention and lubricant additive compositions comprising the same. These fluids include automotive fluids such as manual transmission fluids, automatic transmission fluids, continuously variable transmission fluids, power steering fluids and power brake fluids.

Compounds of the present invention can also be incorporated into greases such as automotive, industrial and aviation greases, and automobile chassis lubricants.

The invention also provides a method of lubricating metal surfaces. Lubricating metal surfaces with lubricant compositions of the present invention can reduce wear between the metal surfaces when moving. In one embodiment, the metal surfaces being lubricated can be a machine part. The machine part can comprise an axle, a differential, an engine, a manual transmission, an automatic transmission, a continuously variable transmission, a clutch, a hydraulic apparatus, an industrial gear, a slideway apparatus, and a turbine.

The invention further provides for a method of lubricating a driveline, industrial, or metalworking device comprising lubricating the driveline, industrial or metalworking device with a lubricant composition comprising a compound of the present invention.

Although certain embodiments of the present invention may be described individually herein, it is understood by the skilled artisan that any one embodiment can be combined with any other embodiment or embodiments, and such combinations are within the scope of the instant invention.

Synthetic Schemes

Certain compounds of the present invention can be prepared using the following generic schemes:

Scheme 1

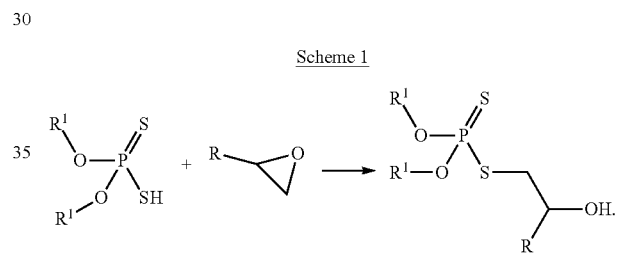

P1a

In certain instances, the synthesis of compounds can result in the production of positional isomers. For example, both primary and secondary alcohols can be formed by a single reaction as follows:

Scheme 2

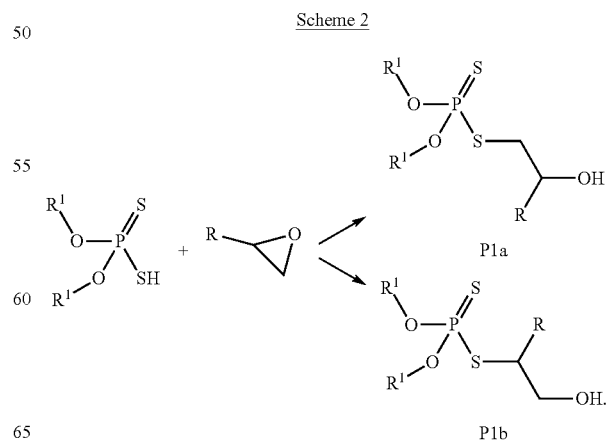

P1a

P1b

-continued
Scheme 3
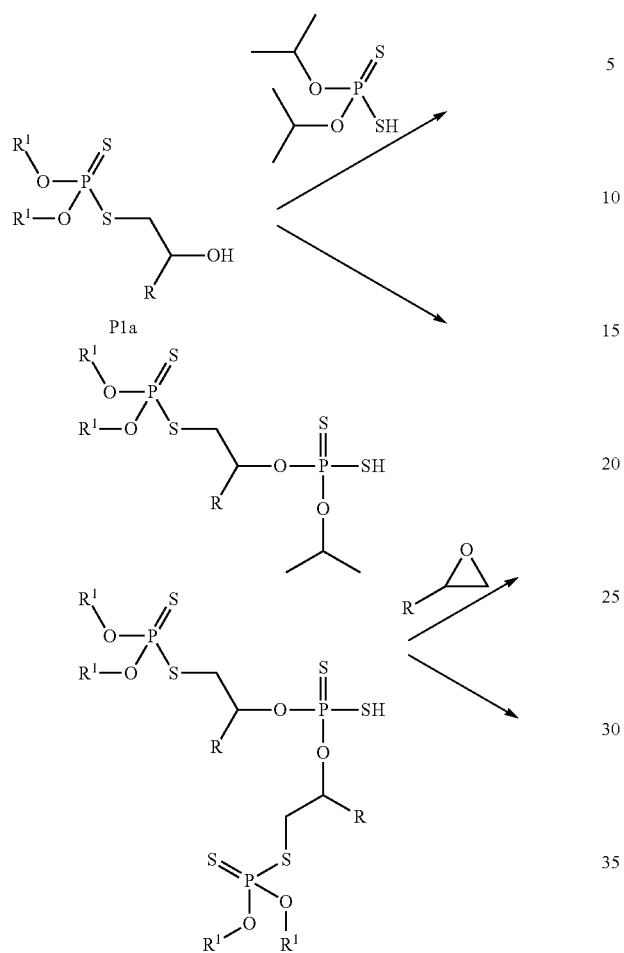
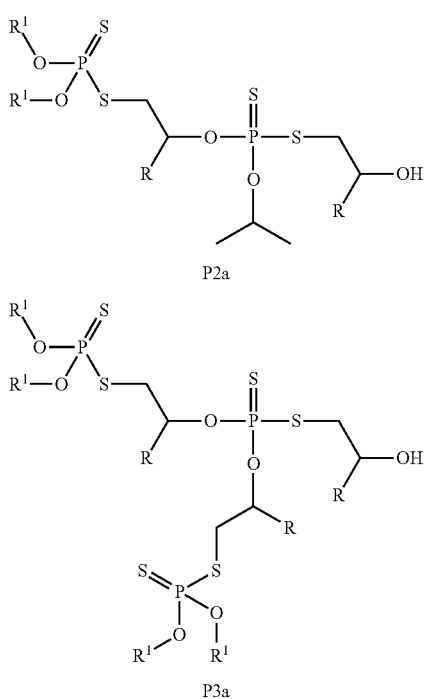
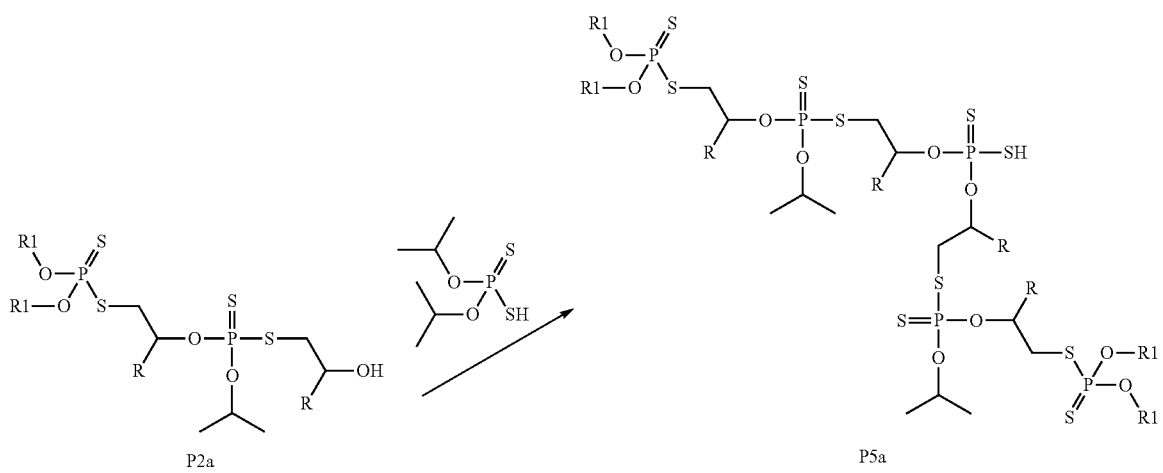

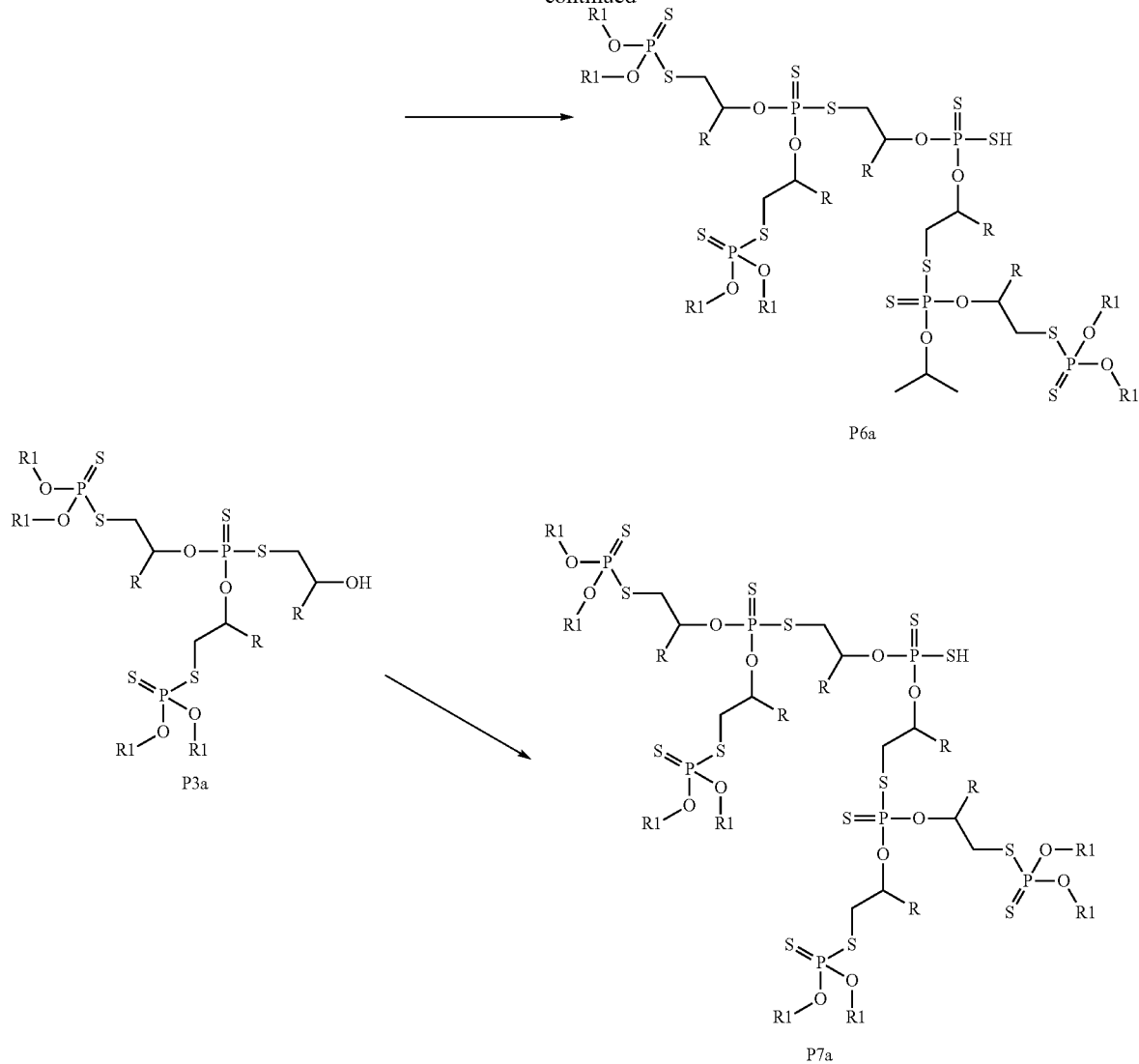

Compounds prepared by the methods illustrated in schemes 2 and 3 can be prepared to enrich certain reaction products. However, in certain embodiments, the reaction products are a mixture of products. For example, the reaction product of the methods described in scheme 2 may be a mixture of the P2a and the P3a product. Similarly, the reaction product from scheme 3 can be a mixture of one or more of the P5a, P6a and P7a product. Likewise, some amount of the reactants may be present in the reaction product. The skilled artisan can readily ascertain the compounds produced from these methods and the mixtures that can result. In the event that a single reaction product is desired, the skilled artisan can employ routine and conventional methods for purifying such reaction products. Purified products and mixtures that result from methods such as those described above are within the scope of the present invention.

The structures shown in the Intermediates and Examples below are the structures of the most abundant isomers produced in the particular reactions described. The skilled artisan appreciates and understands that the above epoxide addition reaction and reactions similar thereto produce compounds as secondary alcohols (P1a). However, the same epoxide addition reaction can form some amount of primary alcohols (P1b). Therefore, the resulting product of the epoxide addition reactions can be a mixture of positional isomers. For the sake of simplicity, only the secondary alcohols and the reaction products therefrom are shown below in Intermediates and Examples. However, all positional isomers of the Intermediates and Examples are within the scope of the invention as a result of these types of reactions.

INTERMEDIATES AND EXAMPLES

The presence of all Intermediates and Examples can be confirmed by 31P NMR, and was confirmed where indicated.

Intermediates

Synthesis of Intermediate P1-A: O,O-bis(4-methylpentan-2-yl) S-hydrogen phosphorodithioate (75.34 g or 0.25 mol) is heated to 40° C. and propylene oxide (14.65 g or 0.25 mol) is added slowly so as to keep the reaction temperature below 50° C. The reaction mixture is then cooked at 50° C. for 30 minutes. Intermediate P1-A is the reaction product and was confirmed by 31P NMR.

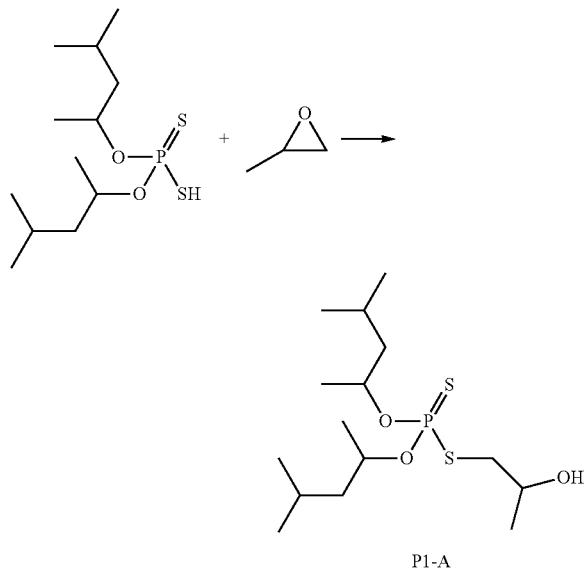

P1-A

Synthesis of Intermediate P1-B: P1-B can be made in a process similar to P1-A except O,O-bis(4-methylpentan-2-yl) S-hydrogen phosphorodithioate is replaced with O,O-bis (isopropyl) S-hydrogen phosphorodithioate. Intermediate P1-B is the reaction product.

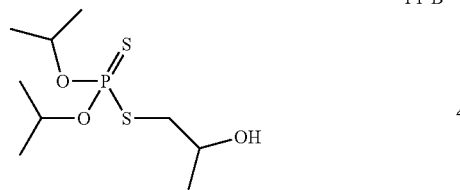

P1-B

Synthesis of Intermediate P1-C: P1-C can be made in a process similar to P1-A except O,O-bis(4-methylpentan-2-yl) S-hydrogen phosphorodithioate is replaced with O,O-bis (2-ethylhexyl) S-hydrogen phosphorodithioate. Intermediate P1-C is the reaction product.

P1-C

Synthesis of Intermediate P1-D: P1-D can be made in a process similar to P1-A except O,O-bis(4-methylpentan-2-yl) S-hydrogen phosphorodithioate is replaced with O,O-bis (isobutyl) S-hydrogen phosphorodithioate. Intermediate P1-D is the reaction product.

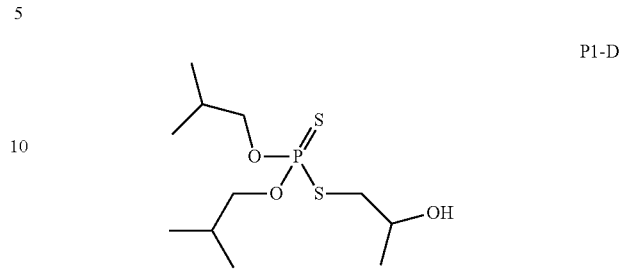

P1-D

Synthesis of Intermediate P3-A: P1-A (600 g, 1.68 moles) was combined with O,O-di-isopropyl dithiophosphoric acid (180 g, 0.84 moles; used as supplied by Cheminova) in a round bottomed flask equipped with a magnetic stirring bar. The reaction contents were heated to 90° C. under reduced pressure (10 mm Hg). Throughout the reaction isopropanol was distilled off and collected into a separate cooled vessel. After 6.5 hours the reaction contents were cooled to 10° C. and propylene oxide (49 g, 0.84 moles; Sigma Aldrich) slowly added to the stirring reaction over a 45 minute period. The presence of P3-A was confirmed by 31P NMR.

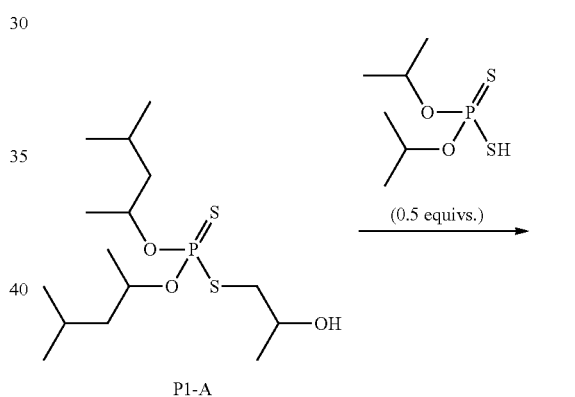

P1-A

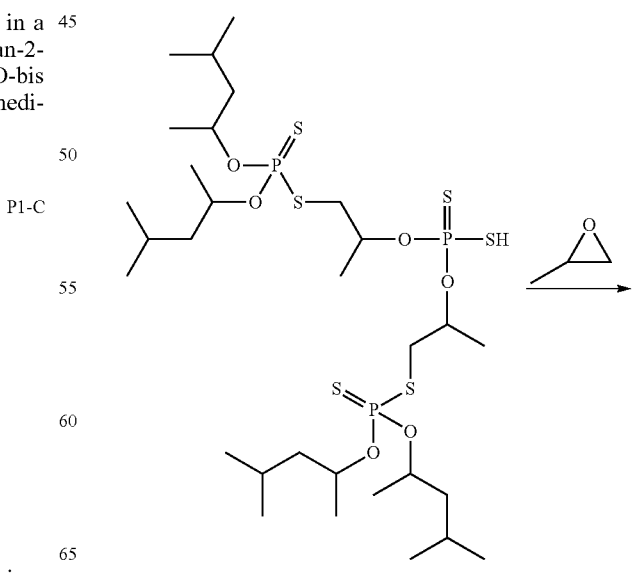

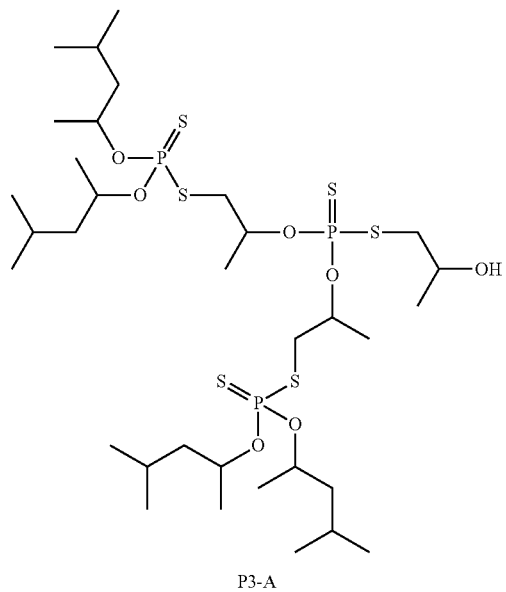

P3-A

Synthesis of Intermediates P3-B, P3-C and P3-D: P3-B, P3-C and P3-D can be prepared similarly to P3-A, with the exception that P1-A is replaced with P1-B, P1-C and P1-D, respectively.

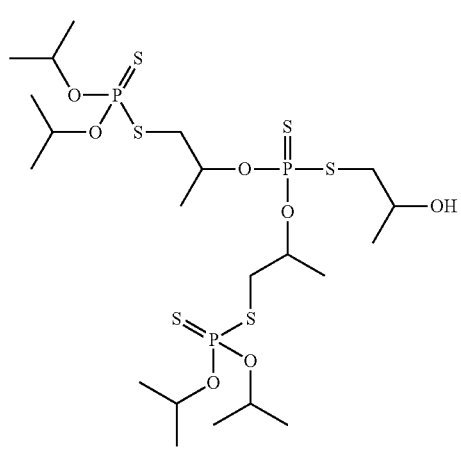

P3-B

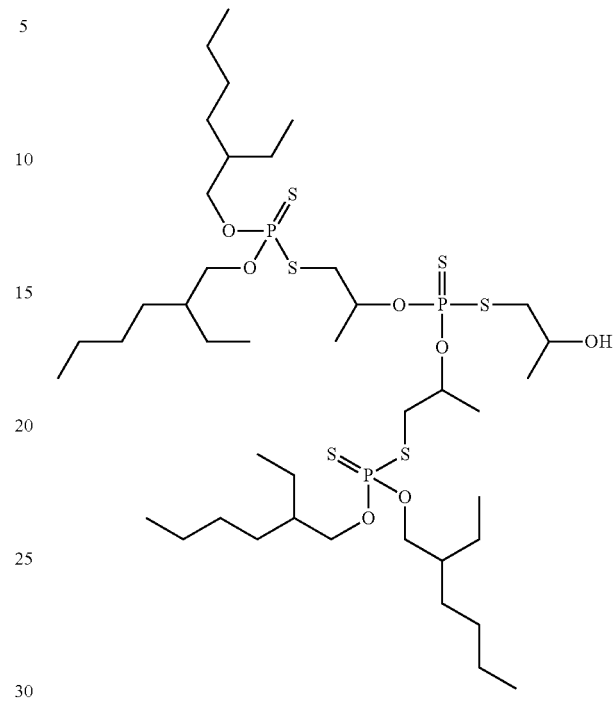

P3-C

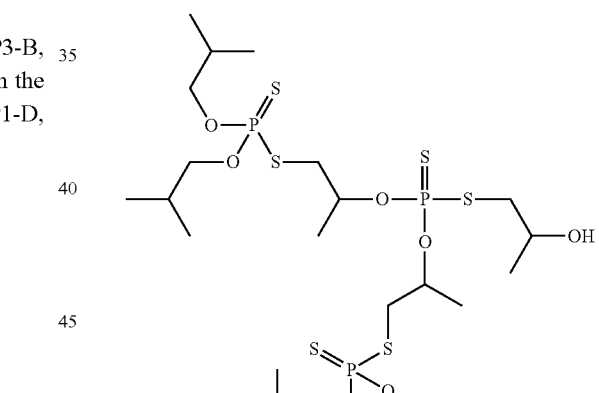

P3-D

Synthesis of Intermediate P4-A: Intermediate P3-A is prepared as above. To the reaction, O,O-di-isopropyl dithiophosphoric acid (376 g, 1.76 moles; used as supplied by Cheminova) was added and the reaction mixture heated at 90° C. and 10 mm Hg of pressure for 6 hours before cooling to room temperature. The presence of P4-A was confirmed by 31P NMR.

Synthesis of Intermediates P4-B, P4-C and P4-D: P4-B, P4-C and P4-D can be made similarly to P4-A, with the exception that P3-A is replaced with P3-B, P3-C and P3-D, respectively.

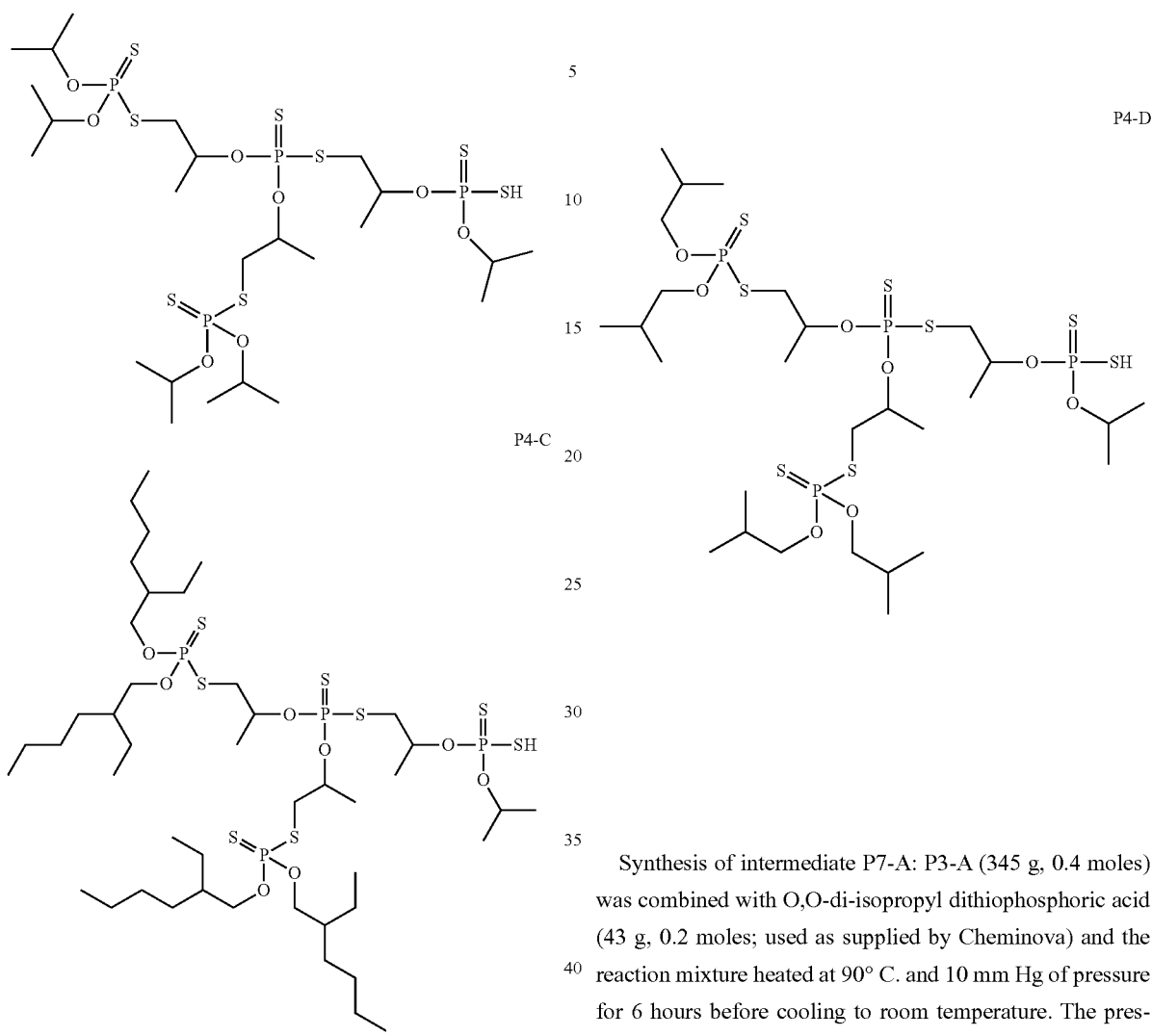
Synthesis of intermediate P7-A: P3-A (345 g, 0.4 moles) was combined with O,O-di-isopropyl dithiophosphoric acid (43 g, 0.2 moles; used as supplied by Cheminova) and the reaction mixture heated at 90° C. and 10 mm Hg of pressure for 6 hours before cooling to room temperature. The presence of P7-A was confirmed by 31P NMR.
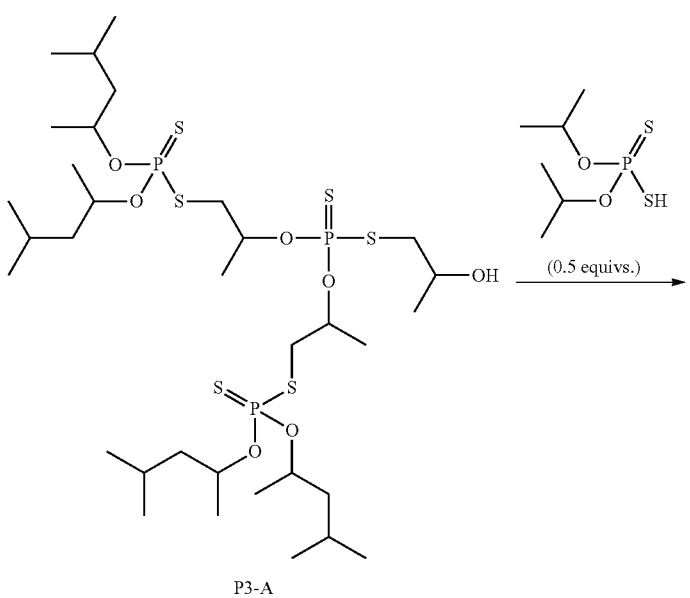

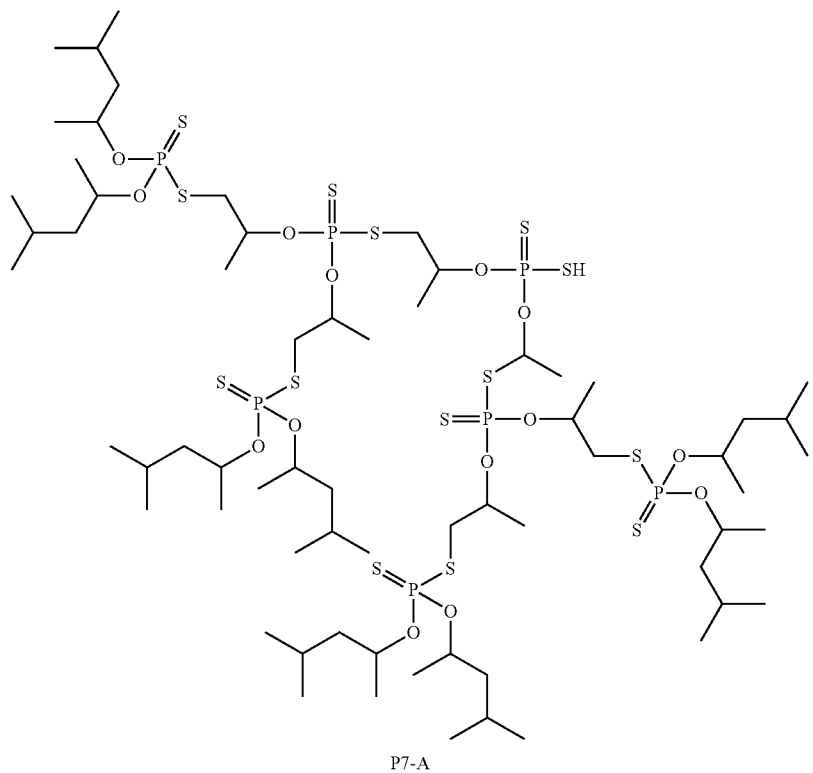
P7-A
Synthesis of intermediates P7-B, P7-C and P7-D: P7-B, P7-C and P7-D can be prepared similarly to P7-A, with the exception that P3-A is replaced with P3-B, P3-C and P3-D, respectively.
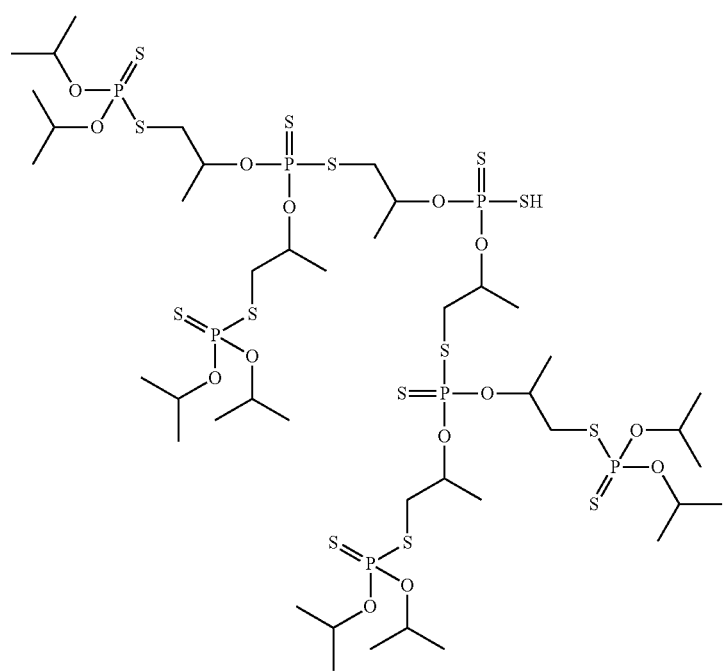
P7-B P7-C
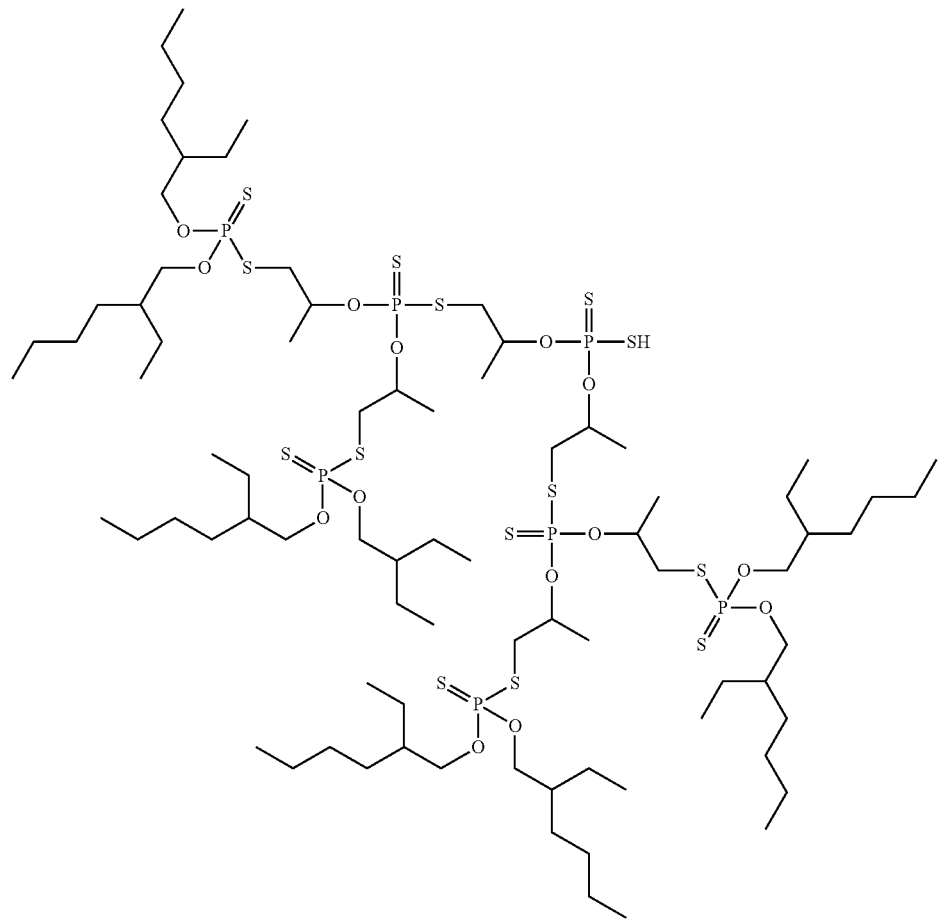
P7-D
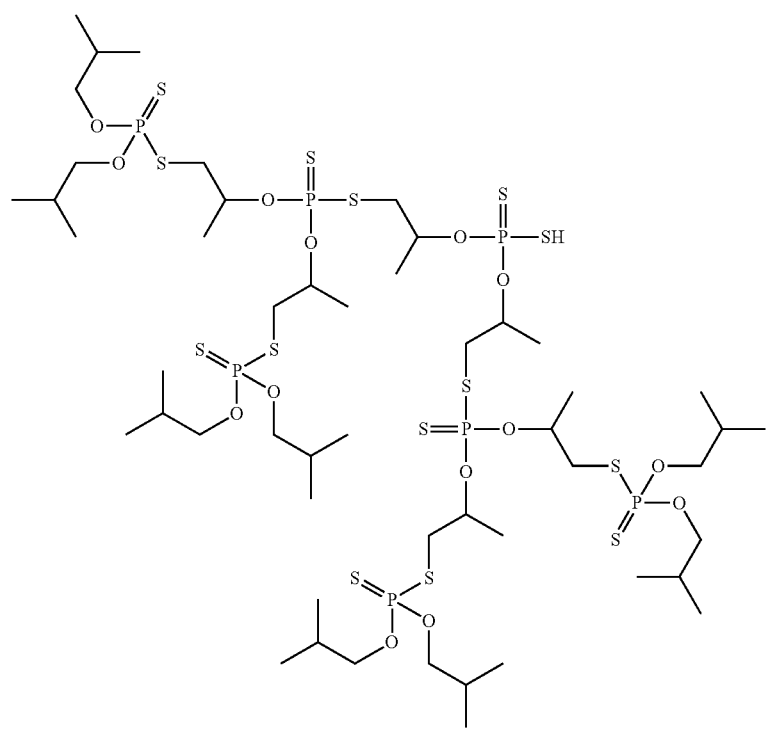

EXAMPLES

Example 1

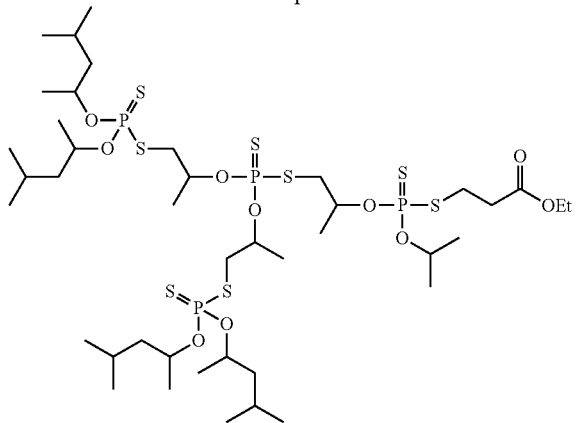

Intermediate P1-A (600 g, 1.68 moles) was combined with O,O-di-isopropyl dithiophosphoric acid (180 g, 0.84 moles; used as supplied by Cheminova) in a round bottomed flask equipped with a magnetic stirring bar. The reaction contents were heated to 90° C. under reduced pressure (10 mm Hg). Throughout the reaction isopropanol was distilled off and collected into a separate cooled vessel. After 6.5 hours the reaction contents were cooled to 10° C. and propylene oxide (49 g, 0.84 moles; Sigma Aldrich) slowly added to the stirring reaction over a 45 minute period. At this time O,O-di-isopropyl dithiophosphoric acid (376 g, 1.76 moles; used as supplied by Cheminova) was added and the reaction mixture heated at 90° C. and 10 mm Hg of pressure for 6 hours before cooling to room temperature. Ethyl acrylate (270 g, 2.7 moles; Dow Chemical) was next added to the reaction and the temperature brought to 70° C. for 2 hours. Subsequently, the reaction was brought to 80° C. and a 100 mm Hg vacuum applied until ethyl acrylate no longer distilled off into the cold trap. The presence of Example 1 was confirmed by 31P NMR.

Example 2

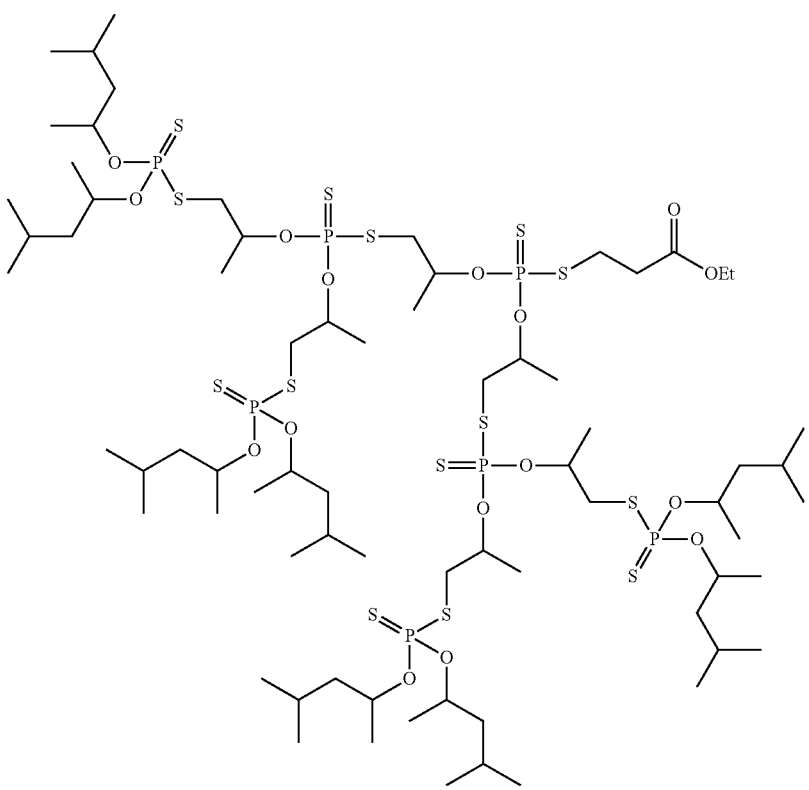

Intermediate P3-A (345 g, 0.4 moles) was combined with O,O-di-isopropyl dithiophosphoric acid (43 g, 0.2 moles; used as supplied by Cheminova) and the reaction mixture heated at 90° C. and 10 mm Hg of pressure for 6 hours before cooling to room temperature. Ethyl acrylate (20 g, 0.2 moles; Dow Chemical) was next added to the reaction and the temperature brought to 70° C. for 2 hours. Subsequently, the reaction was brought to 80° C. and a 100 mm Hg vacuum applied until ethyl acrylate no longer distilled off into the cold trap. The presence of Example 2 was confirmed by 31P NMR.

Example 3

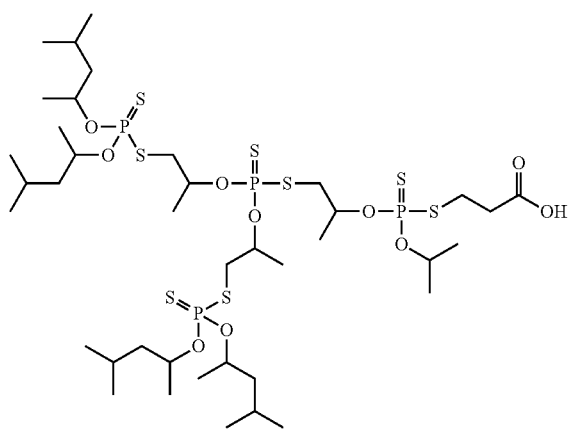

Intermediate P4-A (200 g, 0.2 moles) was combined with acrylic acid (14 g, 0.19 moles) and the reaction left to stir at 70° C. for two hours before applying a 10 mm Hg vacuum to strip off any remaining volatiles. The presence of Example 3 was confirmed by 31P NMR.

Example 4

Intermediate P7-A (200 g, 0.11 moles) was combined with acrylic acid (7.2 g, 0.1 moles) and the reaction left to stir at 70° C. for two hours before applying a 10 mm Hg vacuum to strip off any remaining volatiles. The presence of Example 4 was confirmed by 31P NMR.

Example 5

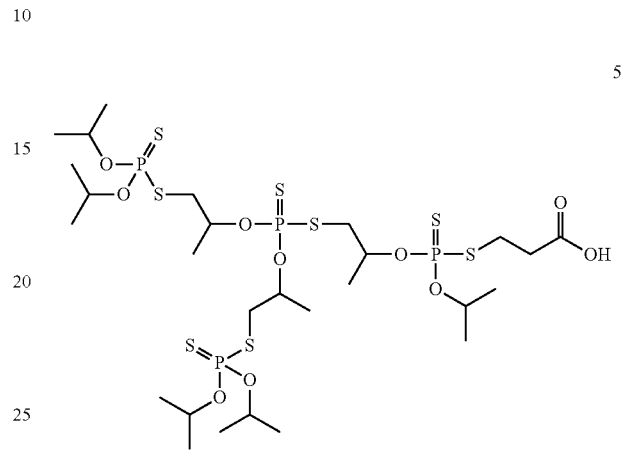

The compound of Example 5 is prepared as in Example 3 except P4-A is replaced with P4-B.

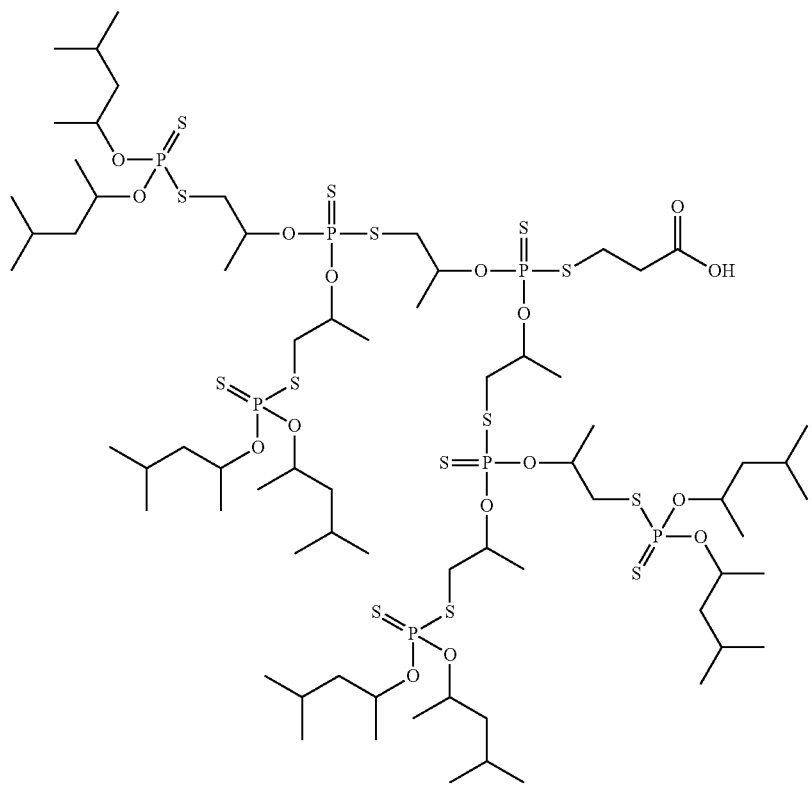

Example 6
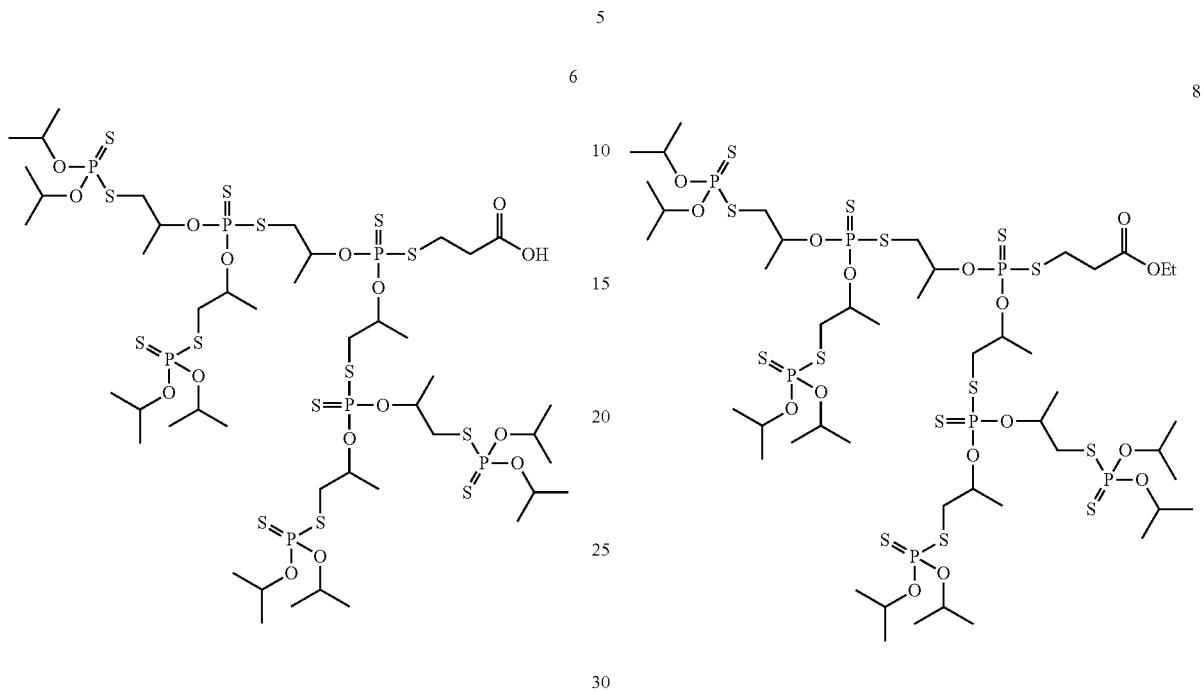
Example 8
The compound of Example 6 is prepared as in Example 4 except P7-A is replaced with P7-B.
The compound of Example 8 is prepared as in Example 2 except P3-A is replaced with P3-B.
Example 7
The compound of Example 7 is prepared as in Example 1 except P1-A is replaced with P1-B.

Example 9
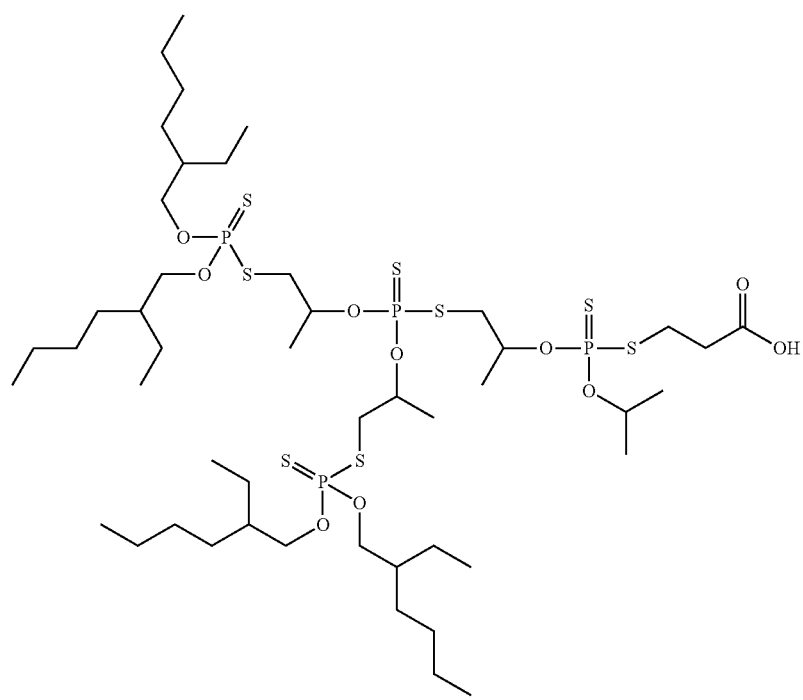
9
The compound of Example 9 is prepared as in Example 3 except P4-A is replaced with P4-C
Example 10
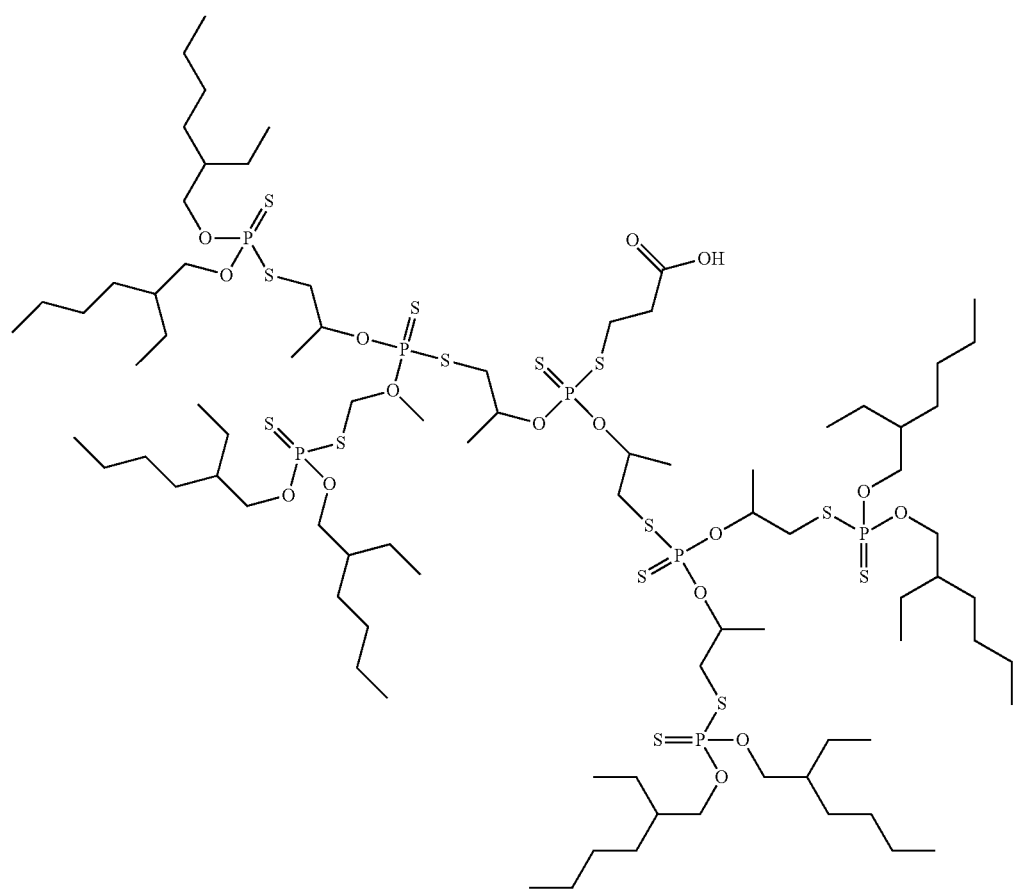
10

The compound of Example 10 is prepared as in Example 4 except P7-A is replaced with P7-C.
Example 11
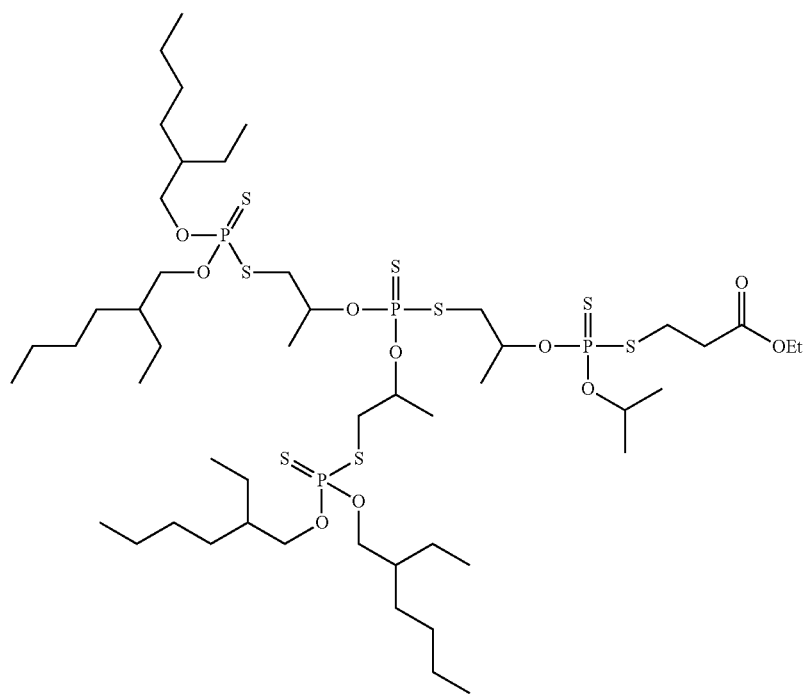
11
The compound of Example 11 is prepared as in Example 1 except P1-A is replaced with P1-C.

Example 12
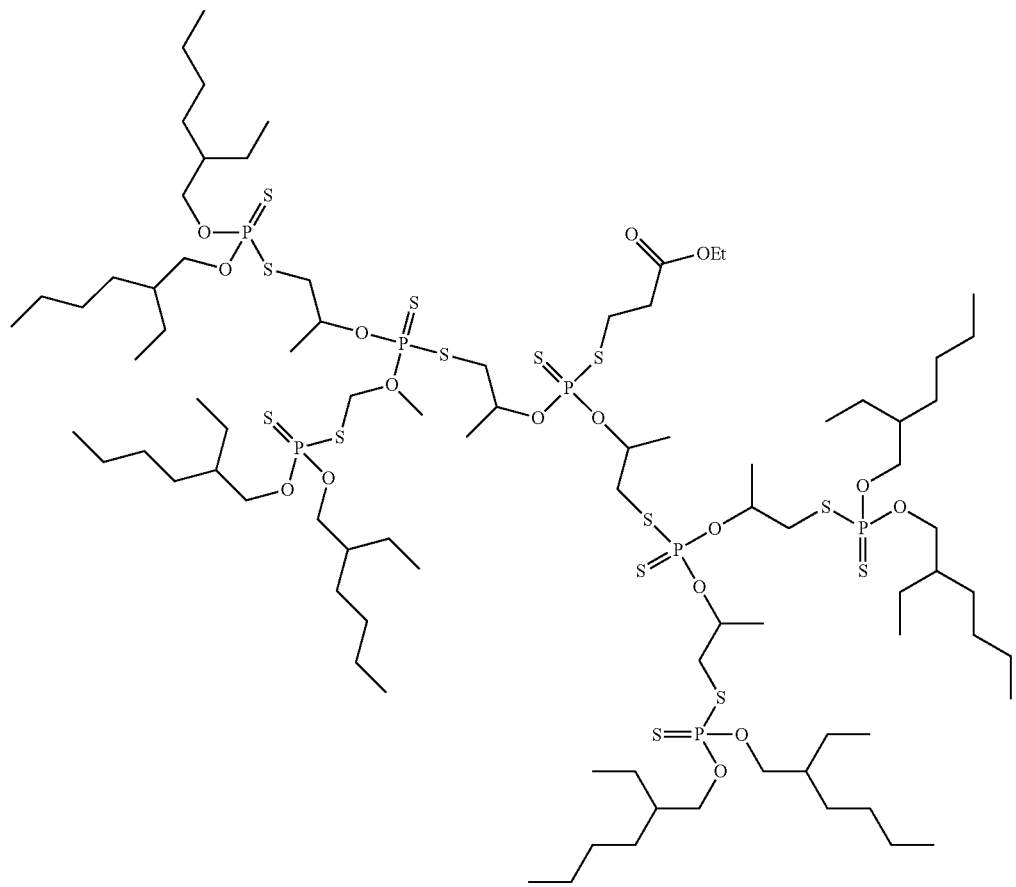
The compound of Example 12 is prepared as in Example 2 except P3-A is replaced with P3-C.
Example 13
Example 14
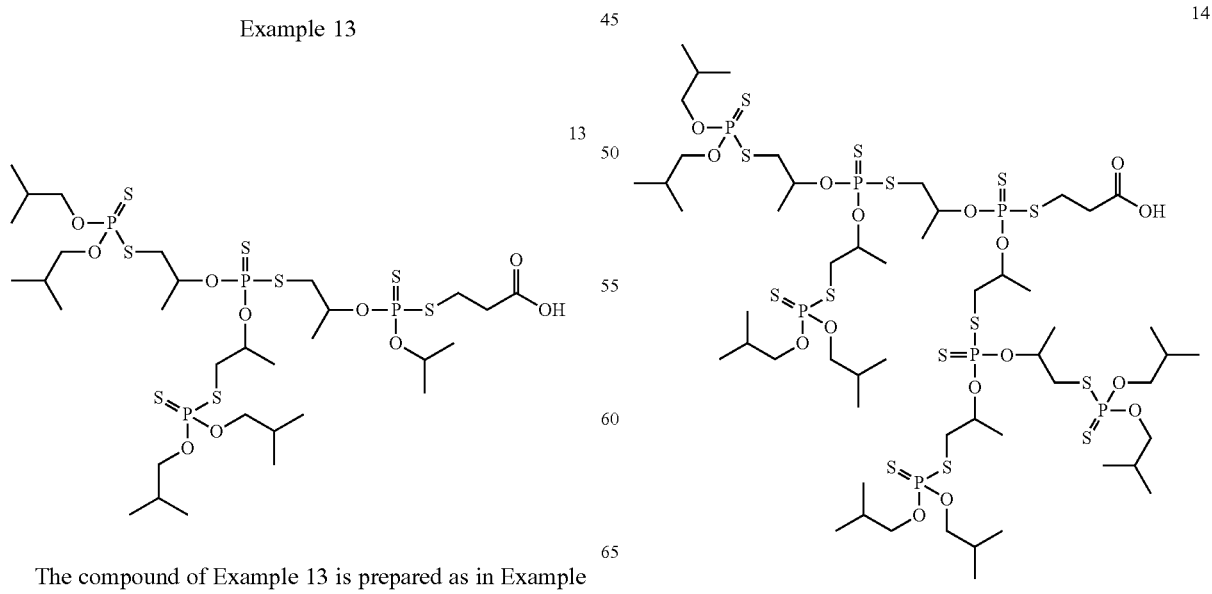
The compound of Example 13 is prepared as in Example 3 except P4-A is replaced with P4-D The compound of Example 14 is prepared as in Example 4 except P7-A is replaced with P7-D.
Example 15
The compound of Example 15 is prepared as in Example 1 except P1-A is replaced with P1-D.
Example 16
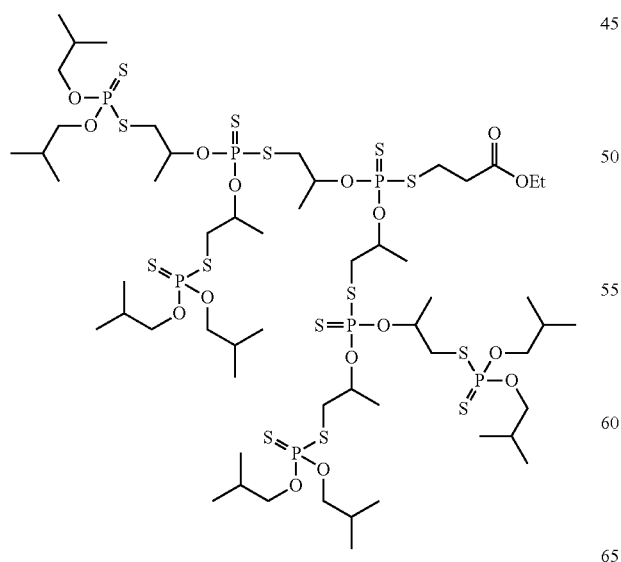
The compound of Example 16 is prepared as in Example 2 except P3-A is replaced with P3-D.
Example 17
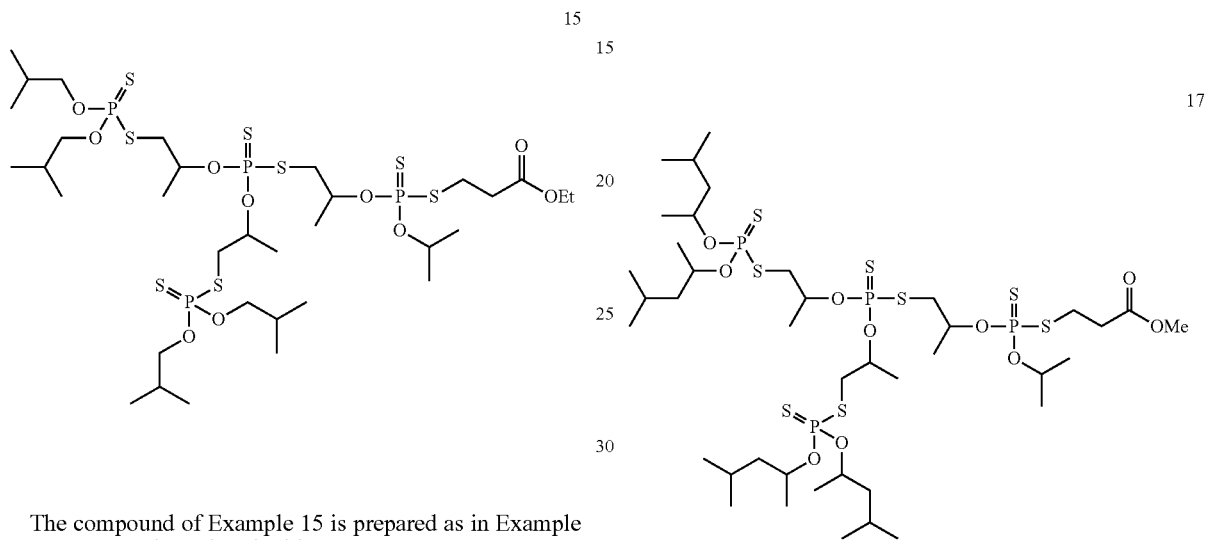
Example 17 is prepared as in Example 1 except the ethyl acrylate is replaced with methyl acrylate.

Example 18
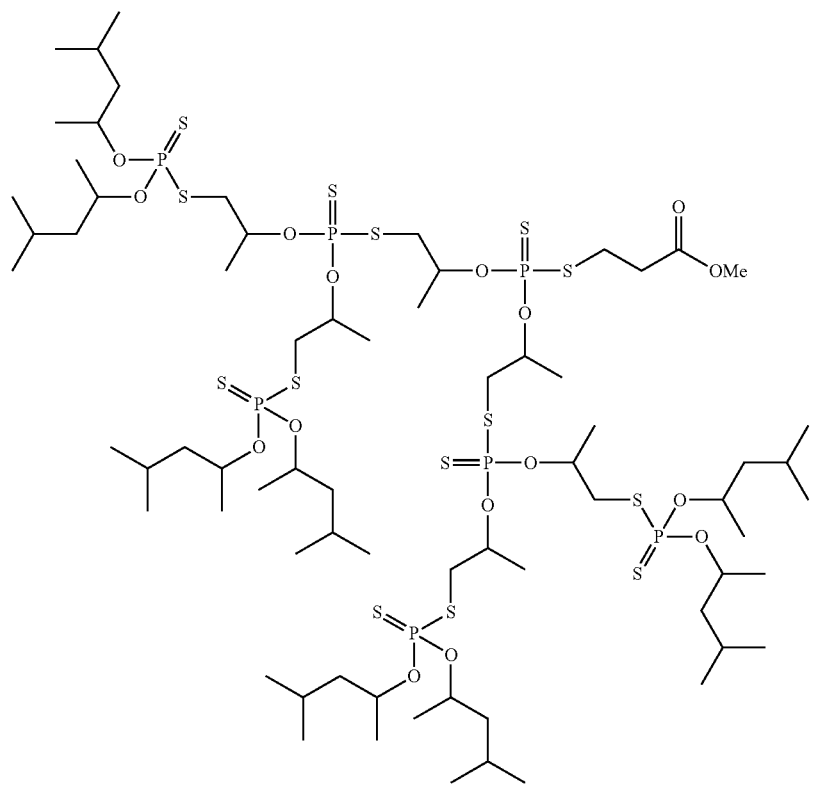
Example 18 is prepared as in Example 2 except the ethyl acrylate is replaced with methyl acrylate.
Example 19
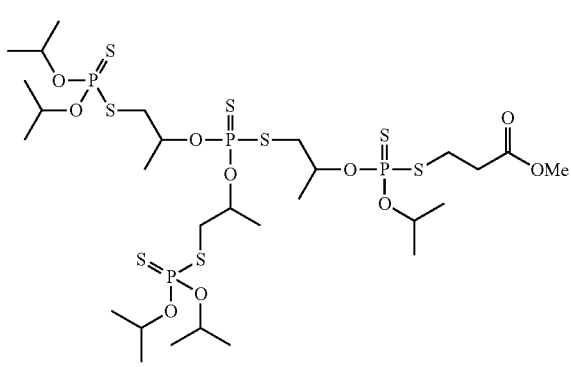
Example 19 is prepared as in Example 7 except the ethyl acrylate is replaced with methyl acrylate.
Example 20
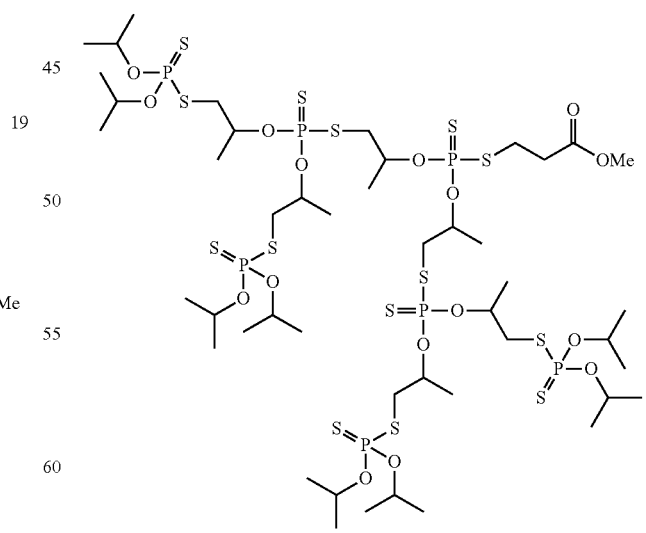
Example 20 is prepared as in Example 8 except the ethyl acrylate is replaced with methyl acrylate.

Example 21
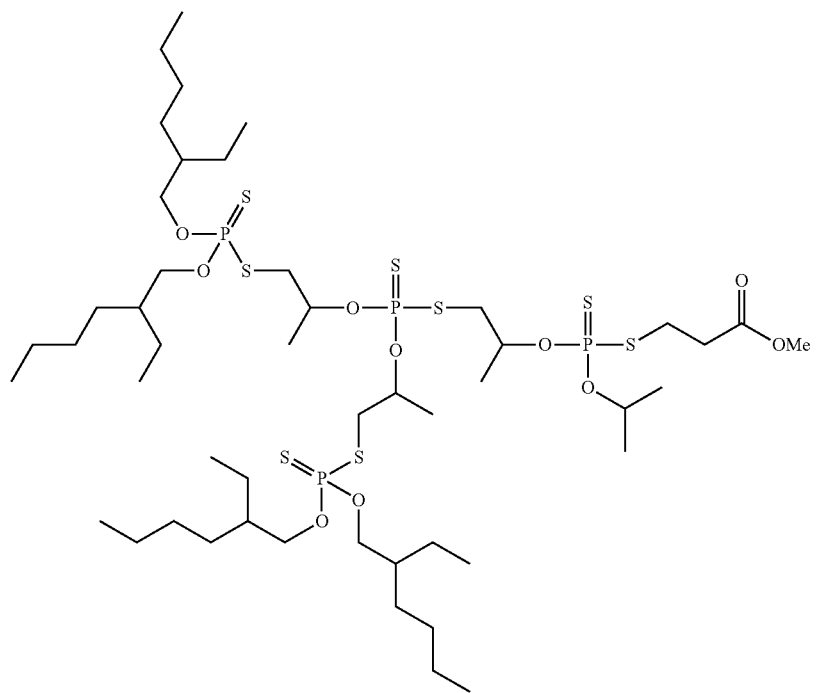
21
Example 21 is prepared as in Example 11 except the ethyl acrylate is replaced with methyl acrylate.

Example 22
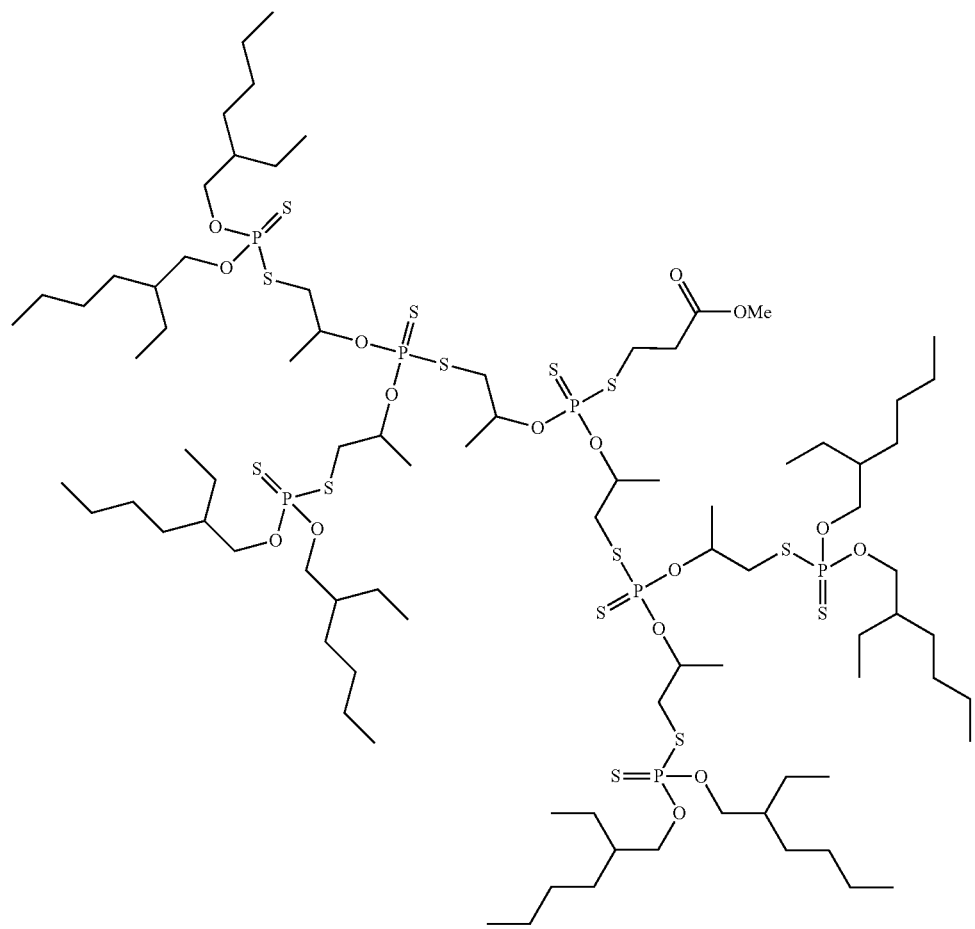
Example 22 is prepared as in Example 12 except the ethyl acrylate is replaced with methyl acrylate.
Example 23
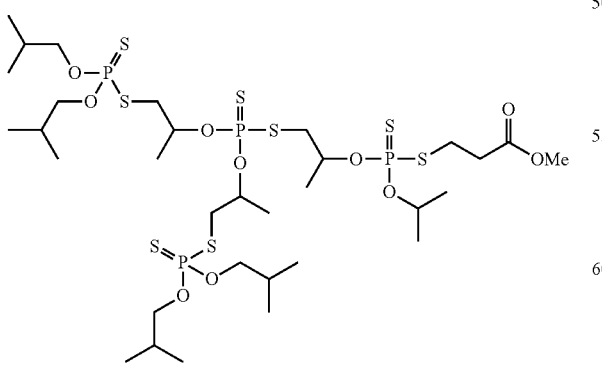
Example 23 is prepared as in Example 15 except the ethyl acrylate is replaced with methyl acrylate.
Example 24
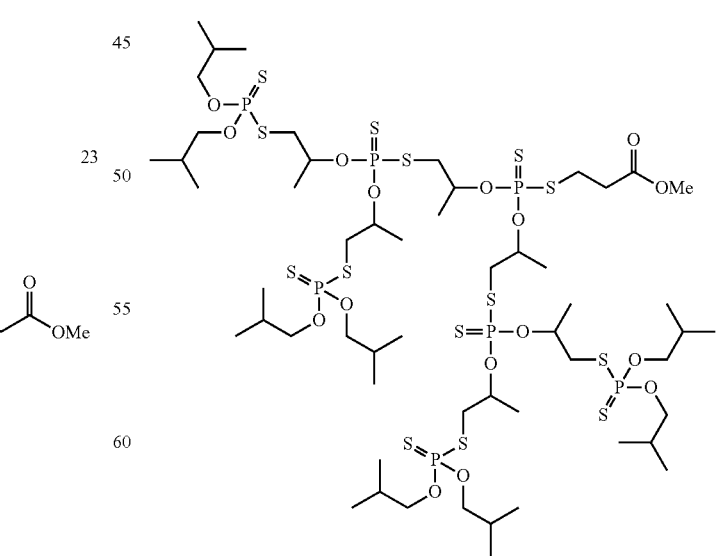
Example 24 is prepared as in Example 16 except the ethyl acrylate is replaced with methyl acrylate.

Example 25

Amine Carboxylate Salt

The compound of Example 3 can be treated with an amine containing compound, for example octylamine or oleylamine, at such a treat rate that TAN=TBN to produce an amine carboxylate salt. The compound of Example 3 can be added to a suitable reaction vessel under stirring. To this the amine containing compound can be added slowly so as to control the exothermic event.

Anti-Wear Performance

Compounds were tested in the four ball wear scar and high temperature L37 tests to determine anti-wear performance. Compounds were individually blended into finished fluids such that a constant level of phosphorous (1100 ppm) was maintained throughout the series. Other than the test compounds, each of the fluids contained a common group of additives employed at equal treat rates. Shown in Table 1 is a summary of the high temperature L37 performance data obtained on these fluids. It can be seen that the ashless dithiophosphate failed the wear test and had end of test iron levels (EOT Fe), as measured by ICP on the used oil, in excess of 5000 ppm. Conversely, compounds of the instant invention, particularly Examples 1 through 4, provide sufficient protection to the gear surfaces that passing test ratings are achieved.

TABLE 1

Summary of High Temperature L37 Wear Performance Data.

| Compound | Fluid Code | HT-L37 Result | EOT Fe, ppm | Ring Ratings | Pinion Ratings |
|---|---|---|---|---|---|
| ashless dithiophosphate* | — | Fail | 5880 | 5/8/6 | 6/8/6 |
| Ex. 1 | R1414317T | Pass | 122 | 8/10/10 | 8/9/8 |
| Ex. 2 | R1414444T | Pass | 127 | 8/10/10 | 7/8/8 |
| Ex. 3 | R14 14318T | Pass | 133 | 8/10/10 | 8/9/9 |
| Ex. 4 | R14 14487T | Pass | 130 | 8/10/10 | 8/9/8 |

*Commercially available as Irgalube 63, typically containing 19.8% sulfur and 8.9% phosphorus, from BASF The samples above were subjected to the High Temperature L-37 test (according to ASTM D-6121), modified to test the lubricant at 325° F. The HT L-37 is used to determine the load-carrying, wear, and extreme pressure characteristics of gear lubricants in hypoid axle assemblies under conditions of high-speed, low-torque, and low-speed, high-torque operation. The procedure's apparatus includes a rear axle assembly, an engine, a transmission, and two large dynamometers. The axle is operated for 100 minutes at 440 axle rpm, 295° F. lubricant temperature, and 9460 lb-in. of torque. The axle is then operated for 16 hours at 80 axle rpm, 325° F. lubricant temperature, and 41,800 lb-in. of torque. The pass/fail criteria require that there be no "significant" distress to the ring and pinion gears in several different wear categories, including wear, rippling, ridging, spalling and scoring.

In Table 1 above, test results for formulations containing Examples 1, 2, 3 and 4 show that the gear distress as measured in the HT-L37 test was identified by a "pass" test result. A "pass" indicates that significant gear distress was not observed at the end of test. Thus, there was not a significant amount of iron detected in the test sample after completion of the test. When iron is present in the end of test fluid in significant amounts, it is evidence of gear distress and loss of anti-wear protection. All finished fluids used for HT-L37 testing contained sufficient anti-wear to deliver 1100 ppm phosphorus to the finished fluid. The finished fluids only differed in the antiwear component present, but otherwise contained identical formulations of typical axle componentry and base stock. The formulations for the HT-L-37 testing contained 3.24% sulfurized isobutylene, 1.4% of a pour point depressant, 1% boronated maleated bis-succinimide dispersant made with 1300MW polyisobutylene, 0.15% 2,5-(t-nonylthio)-1,3,4-thiadiazole, 0.05% antifoam, 0.005% dimer acid, 1.15% antiwear compound of the present invention, and the balance was a base oil mixture of 150N and 2500N from ExxonMobil in a 35:54 ratio. The 150N has a kinematic viscosity at 40° C. of 29-32 m²/sec. And the 2500N has a kinematic viscosity at 100° C. of 30.6-32.7 mm²/sec. The finished fluid including the base oils and the additive components had a kinematic viscosity at 100° C. of 15.5 cSt.

Other embodiments of the present disclosure will be apparent to those skilled in the art from consideration of the specification and practice of the embodiments disclosed and suggested herein. It is intended that the specification and examples be considered as exemplary only, with a true scope and spirit of the disclosure being indicated by the following claims.

The invention claimed is:

1. A compound of formula (I)

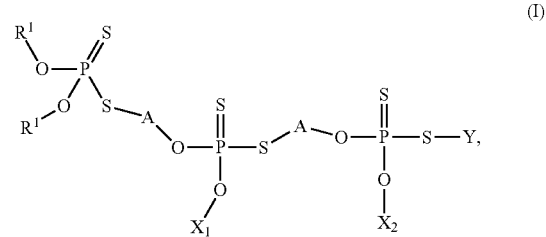

or a tribologically acceptable salt thereof,
wherein A is:

each $R^1$ is the same or different and is independently selected from alkyl, alkenyl, cycloalkyl, cycloalkylalkyl, aryl, and aralkyl, wherein said aryl and aralkyl are optionally substituted with one to three substituents each independently selected from alkyl and alkenyl;

each $R^2$ and $R^3$ are independently selected from H, alkyl, alkenyl, cycloalkyl and cycloalkylalkyl;

Y is selected from the group consisting of alkyl, alkoxyalkyl, benzyl, and —$R^4$-$R^5$-$R^6$;

$R^4$ is alkylene;

$R^5$ is selected from the group consisting of a bond, alkylene; —C(O)— and —C($R^7$)—;

R6 is selected from the group consisting of alkyl, hydroxyalkyl, hydroxyalkyleneoxy, hydroxy and alkoxy, $R^7$ is hydroxy;

m is an integer from 2 to 8;

$X_1$ is $R^8$ or Z;

$X_2$ is selected from the group consisting of $R^8$,

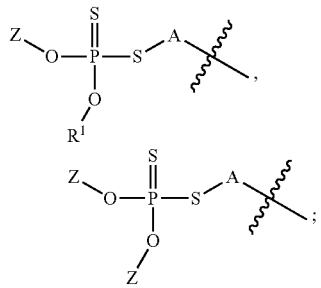 and

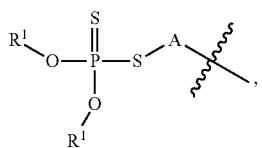;

$R^8$ is alkyl, alkenyl, cycloalkyl, cycloalkylalkyl, aryl, and aralkyl, wherein said aryl and aralkyl are optionally substituted with one to three substituents each independently selected from alkyl and alkenyl; and Z is

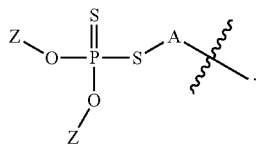, wherein when $X_2$ is $R^8$, $X_1$ is Z.

2. The compound of claim 1, wherein each $R^1$ is the same or different and is independently selected from $C_1$-$C_{30}$alkyl, $C_1$-$C_{30}$alkenyl, cycloalkyl, cycloalkylalkyl, aryl and aralkyl, wherein said aryl and aralkyl are optionally substituted with one to three substituents each independently selected from $C_1$-$C_{10}$alkyl and $C_1$-$C_{10}$alkenyl.

3. The compound of claim 2, wherein each $R^1$ is the same or different and is independently $C_3$-$C_{10}$alkyl.

4. The compound of claim 1, wherein m is 2.

5. The compound of claim 1, wherein for each A, each $R^2$ and $R^3$ are independently selected from H and $C_1$-$C_{10}$alkyl.

6. The compound of claim 5, wherein for each A, one $R^2$ is alkyl and the remaining instances of $R^2$ and $R^3$ are H.

7. The compound of claim 6, wherein $R^2$ is $C_1$-$C_{10}$alkyl.

8. The compound of claim 1, wherein $X_2$ is

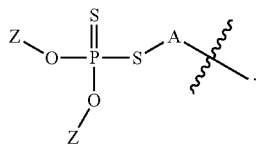.

9. The compound of claim 1, wherein $X_2$ is $R^8$.

10. The compound of claim 1, wherein Y is —$R^4$-$R^5$-$R^6$.

11. The compound of claim 10, wherein $R^4$ is alkylene, $R^5$ is —C(O)—, and $R^6$ is hydroxy or alkoxy.

12. The compound of claim 1, wherein $R^8$ is $C_1$-$C_{10}$ alkyl.

13. The compound of claim 1, wherein the compound is a compound of formula (Ia)

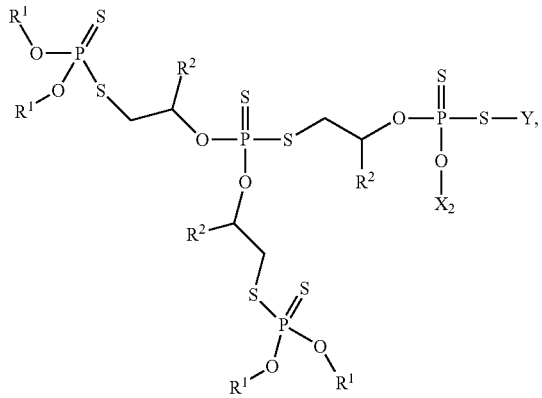

or a tribologically acceptable salt thereof, each $R^1$ is the same or different and is independently selected from alkyl, alkenyl, cycloalkyl, cycloalkylalkyl, aryl, and aralkyl, wherein said aryl and aralkyl are optionally substituted with one to three substituents each independently selected from alkyl and alkenyl;

each $R^2$ is independently selected from alkyl, alkenyl, cycloalkyl and cycloalkylalky;

Y is selected from the group consisting of alkyl, alkoxyalkyl, benzyl, and —$R^4$-$R^5$-$R^6$;

$R^4$ is alkylene;

$R^5$ is selected from the group consisting of a bond, alkylene; —C(O)— and —C($R^7$)—;

$R^6$ is selected from the group consisting of alkyl, hydroxyalkyl, hydroxyalkyleneoxy, hydroxy and alkoxy;

$R^7$ is hydroxy;

$X_2$ is selected from the group consisting of $R^8$,

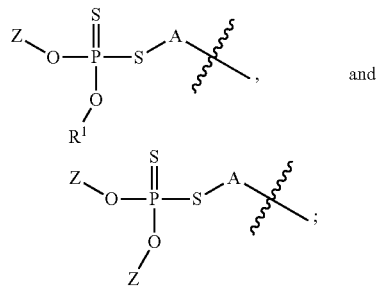 and

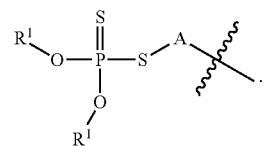.

$R^8$ is alkyl, alkenyl, cycloalkyl, cycloalkylalkyl, aryl, and aralkyl, wherein said aryl and aralkyl are optionally substituted with one to three substituents each independently selected from alkyl and alkenyl; and Z is

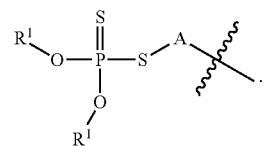.

14. The compound of claim 13, wherein each $R^1$ is the same or different and is independently $C_3$-$C_{10}$alkyl.

15. The compound of claim 13, wherein each $R^2$ is the same or different and is independently $C_1$-$C_{10}$alkyl.

16. The compound of claim 13, wherein $X_2$ is $R^8$ or

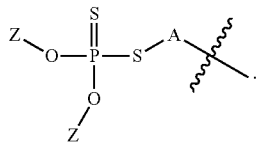

17. The compound of claim 13, wherein $R^8$ is $C_3$-$C_{10}$alkyl.

18. The compound of claim 14, wherein each $R^1$ is the same.

19. The compound of claim 15, wherein each $R^2$ is the same.

20. The compound of claim 13, wherein Y is —$R^4$-$R^5$-$R^6$.

21. The compound of claim 20, wherein $R^4$ is alkylene, $R^5$ is —C(O)—, and $R^6$ is hydroxy or alkoxy.

22. The compound of claim 1, selected from:

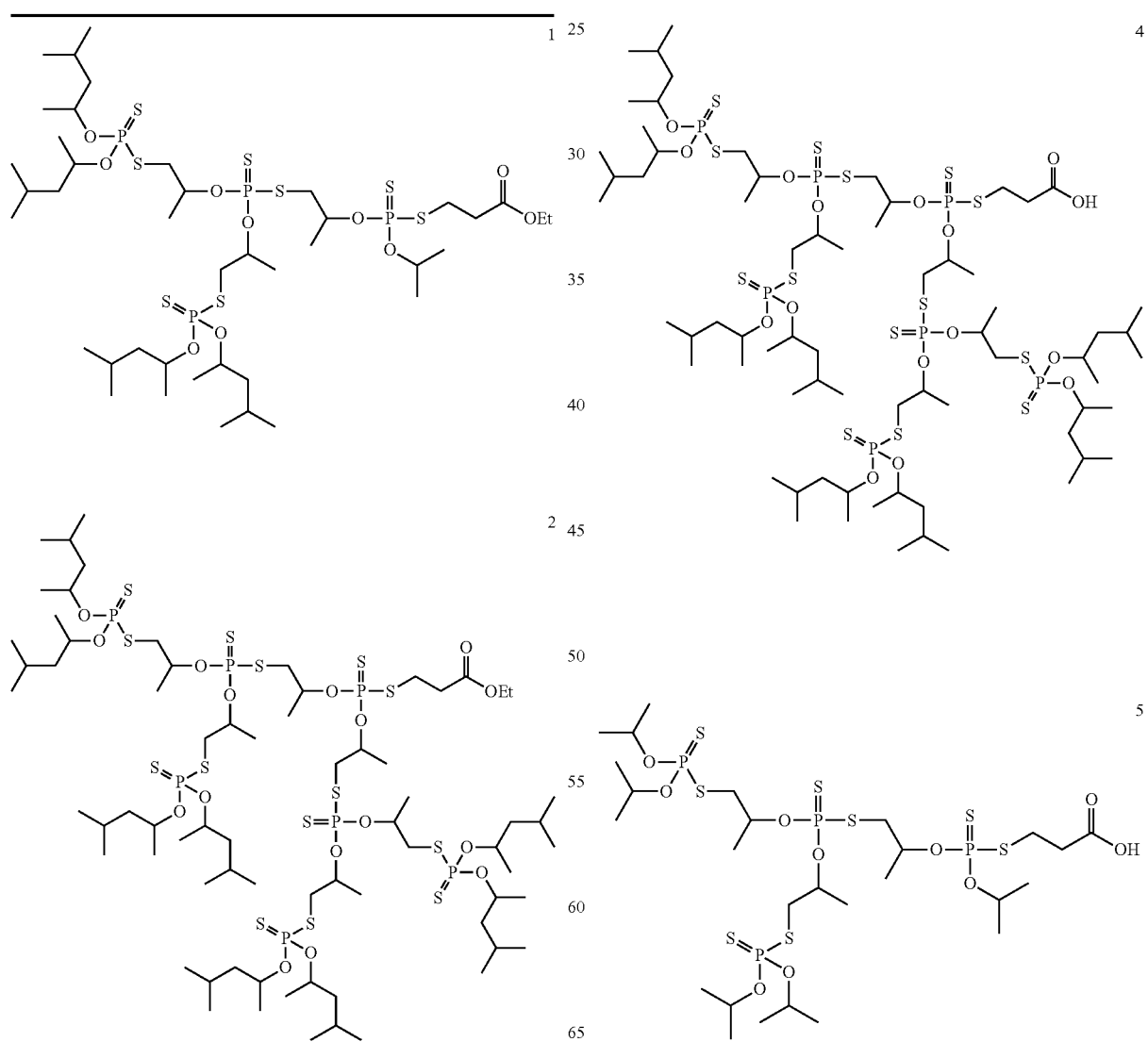

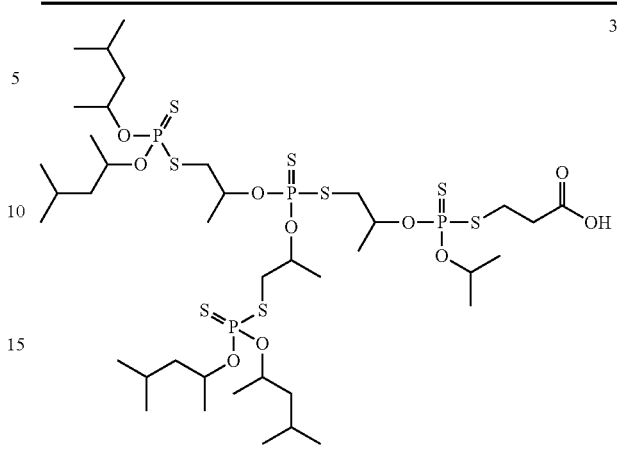

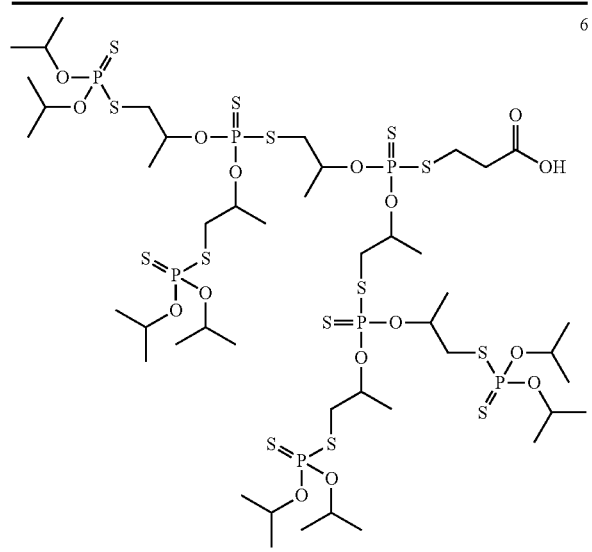
6
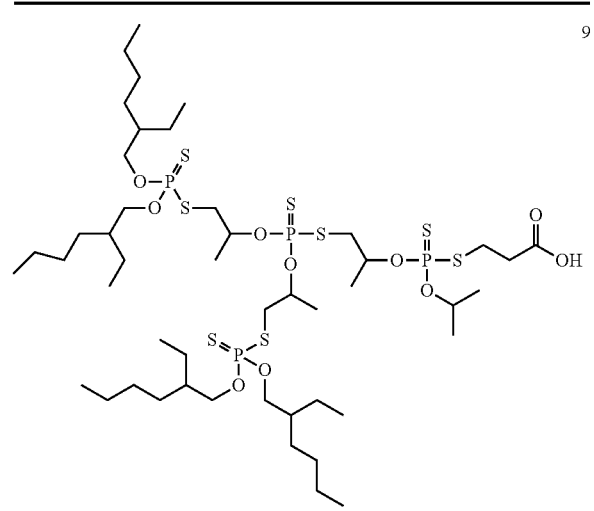
9
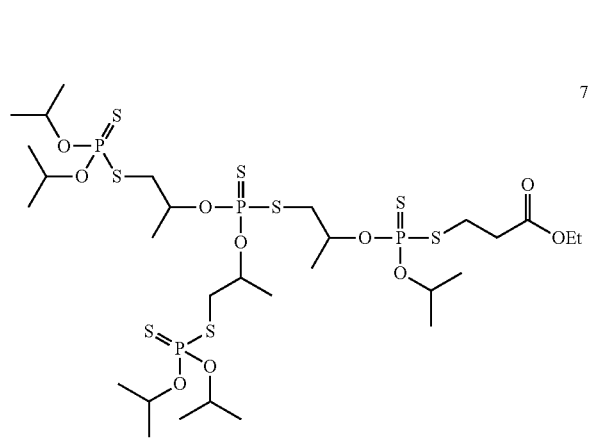
7
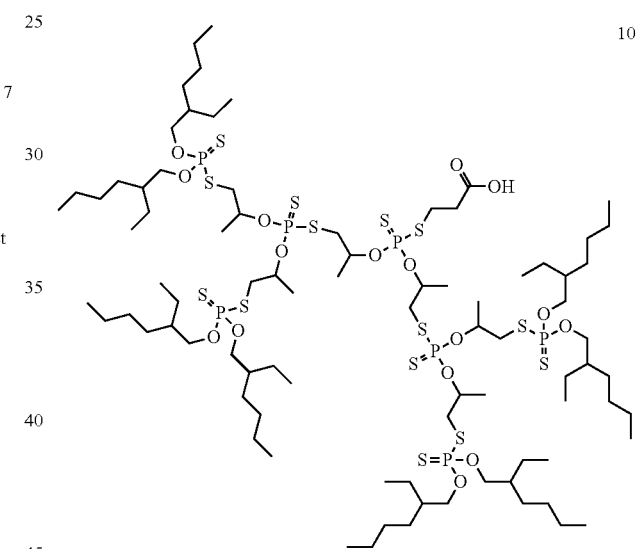
10
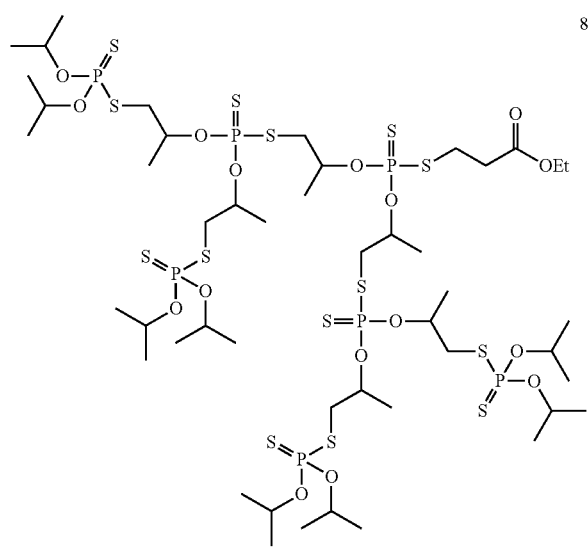
8
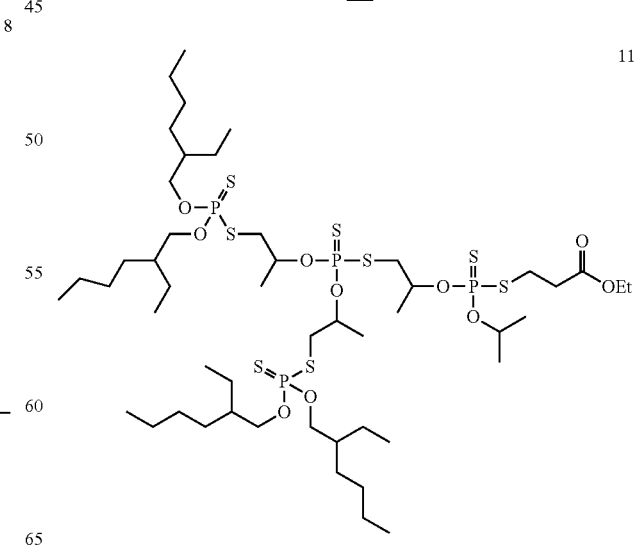
11

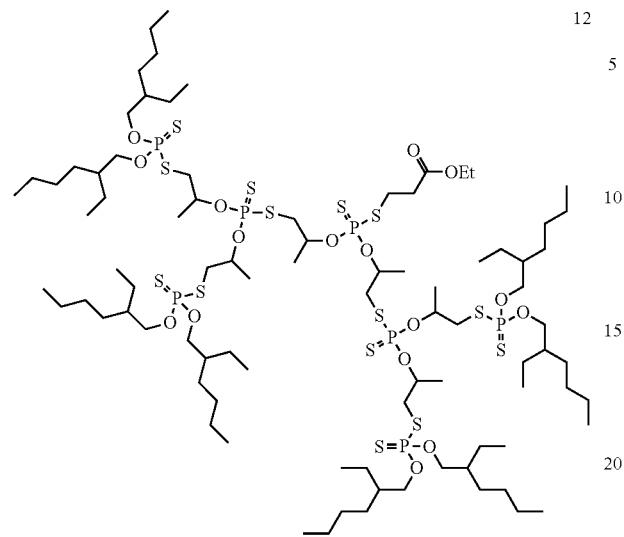
12
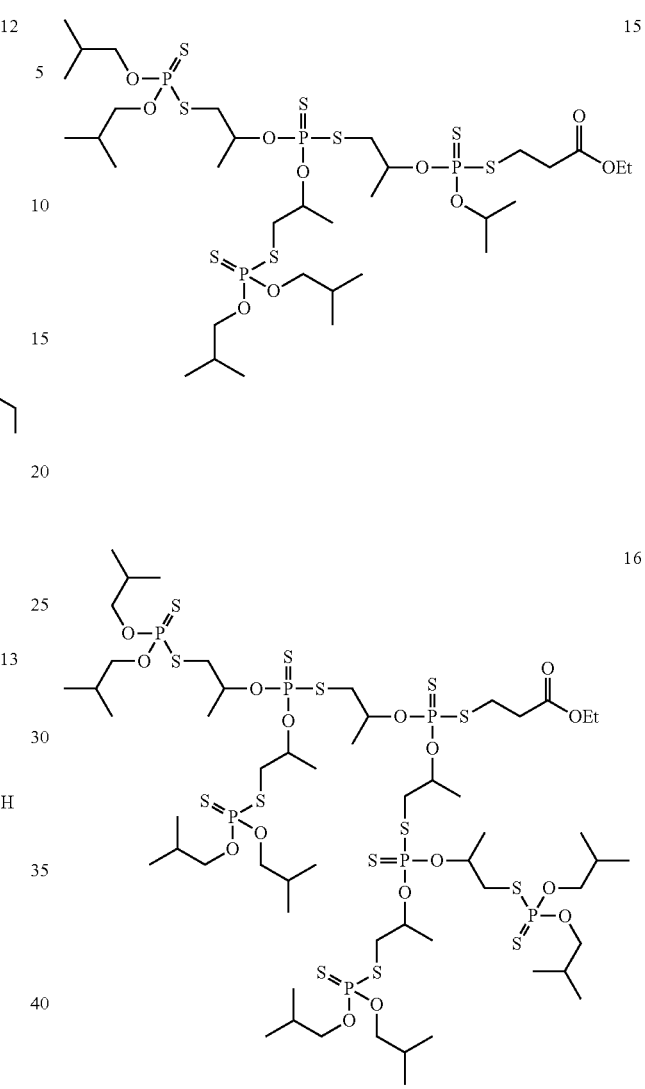
15
13
16
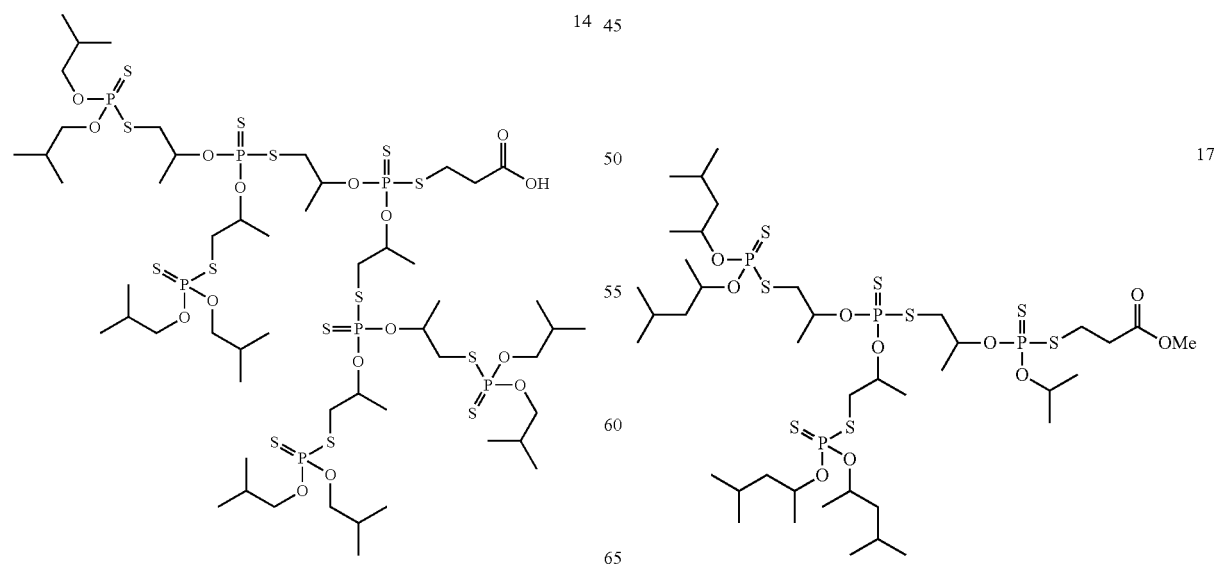
14
17

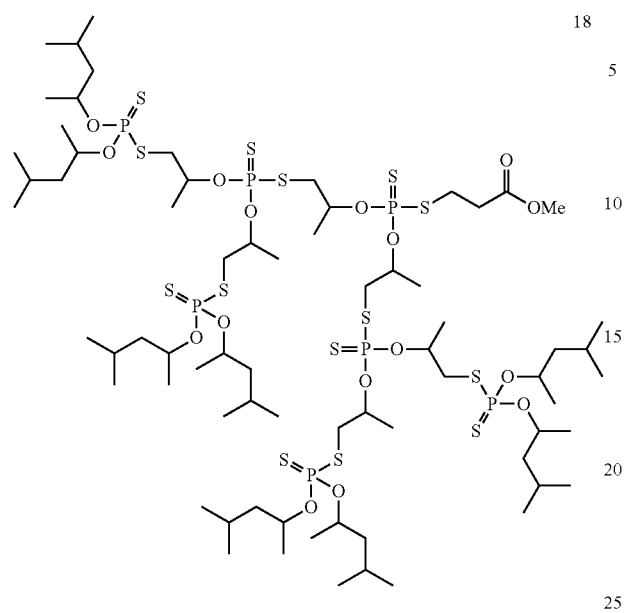
18
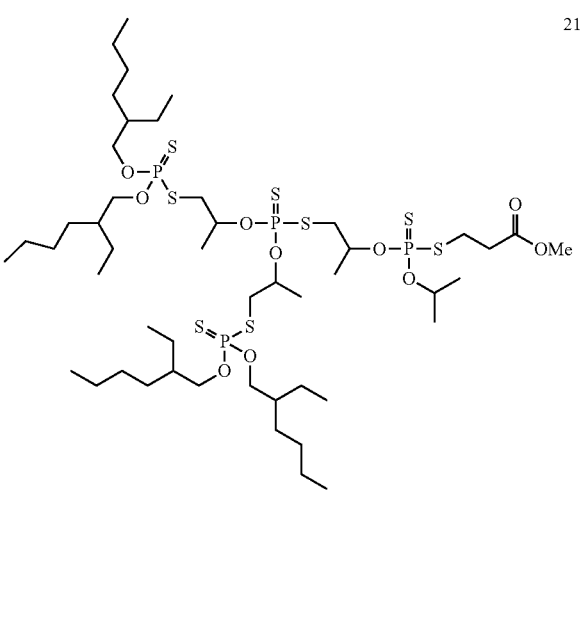
21
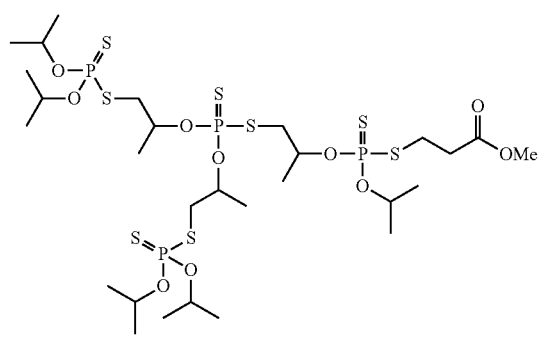
19
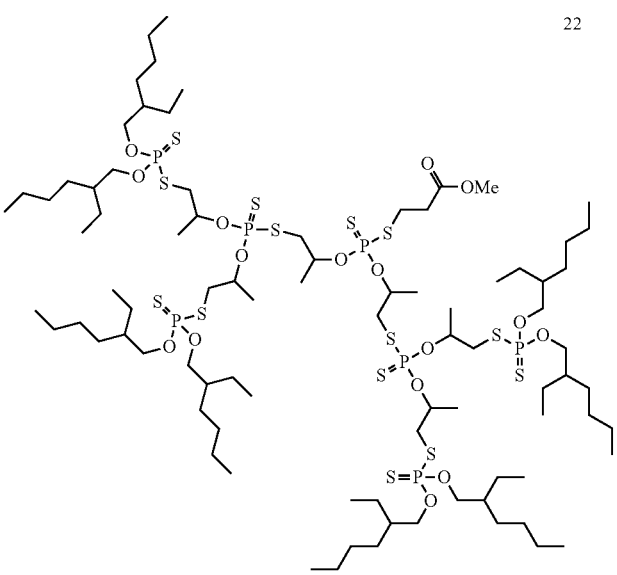 [SMILES: CCCCC(CC)COP(=S)(OCC(CC)CCCC)SCC(C)OP(=S)(OC(C)CSP(=S)(OCC(CC)CCCC)OCC(CC)CCCC)SCC(C)OP(=S)(OC(C)CSP(=S)(OC(C)CSP(=S)(OCC(CC)CCCC)OCC(CC)CCCC)OC(C)CSP(=S)(OCC(CC)CCCC)OCC(CC)CCCC)SCCC(=O)O]
22
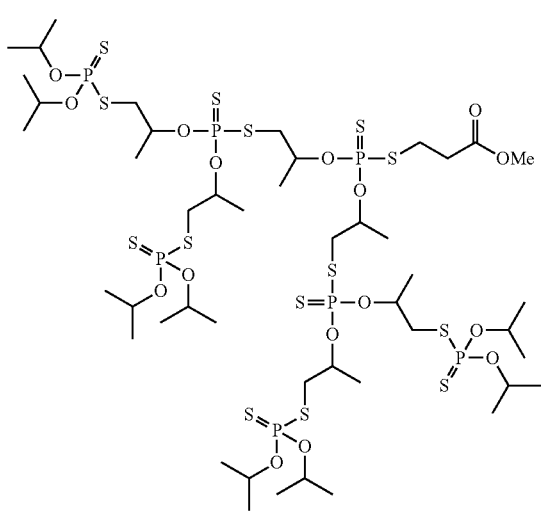 [SMILES: COC(=O)CCSP(=S)(OC(C)CSP(=S)(OC(C)CSP(=S)(OC(C)C)OC(C)C)OC(C)CSP(=S)(OC(C)C)OC(C)C)OC(C)CSP(=S)(OC(C)CSP(=S)(OC(C)C)OC(C)C)OC(C)CSP(=S)(OC(C)C)OC(C)C]
20
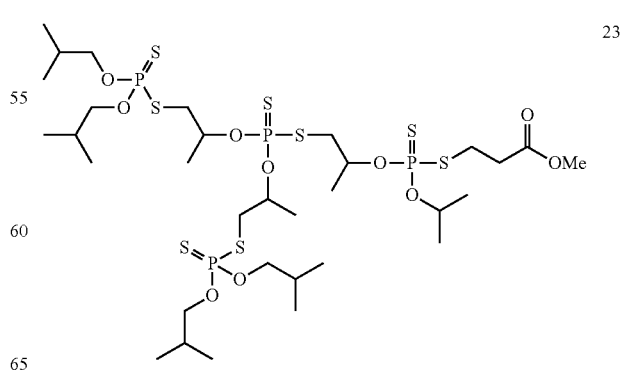
23

-continued

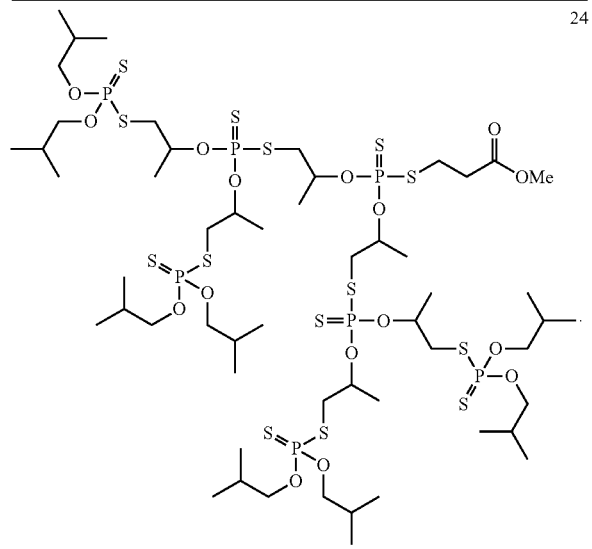

24

23. A lubricant additive composition comprising a compound of claim 1.

24. The lubricant additive composition of claim 23, wherein the lubricant additive composition further comprises one or more additive components selected from the group consisting of an antioxidant, antiwear agents, corrosion inhibitor, detergent, extreme pressure agent, dispersant, viscosity index improvers, and friction modifiers.

25. A lubricant composition comprising:
   a) a base oil; and
   b) a compound as claimed in claim 1,
   wherein the base oil is a major amount of the composition.

26. The lubricant composition of claim 25, wherein the lubricant composition further comprises one or more additive components selected from the group consisting of an antioxidant, antiwear agents, corrosion inhibitor, detergent, extreme pressure agent, dispersant, viscosity index improvers, and friction modifiers.

27. The lubricant composition of claim 26, wherein the compound is present in an amount from about 0.010 wt % to about 5 wt % based on the total weight of the lubricant composition.

28. A method of lubricating moving metal surfaces comprising lubricating the metal surfaces with a lubricant composition of claim 25.

29. The method of claim 28 wherein the moving metal surface is selected from one or more of a gear, an axle, a differential, an engine, a crankshaft, a transmission, a clutch, a hydraulic apparatus, a slideway apparatus, and a turbine.

30. A method of reducing wear between moving metal surfaces of a machine part comprising lubricating the machine part with a lubricant composition comprising:
   a) a major amount of an oil of lubricating viscosity; and
   b) an effective amount of a compound of claim 1.

* * * * *